United States Patent
Dastmalchi et al.

(10) Patent No.: US 10,362,935 B2
(45) Date of Patent: Jul. 30, 2019

(54) USER INTERFACE FOR EFFICIENTLY DISPLAYING RELEVANT OCT IMAGING DATA

(71) Applicant: Carl Zeiss Meditec, Inc., Dublin, CA (US)

(72) Inventors: Shahram Shawn Dastmalchi, San Ramon, CA (US); Jochen Straub, Pleasanton, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 95 days.

(21) Appl. No.: 15/608,239

(22) Filed: May 30, 2017

(65) Prior Publication Data

US 2017/0258321 A1    Sep. 14, 2017

Related U.S. Application Data

(60) Continuation of application No. 15/289,403, filed on Oct. 10, 2016, which is a continuation of application
(Continued)

(51) Int. Cl.
| | |
|---|---|
| G06T 15/08 | (2011.01) |
| A61B 3/00 | (2006.01) |
| A61B 3/10 | (2006.01) |
| G06F 19/00 | (2018.01) |
| G06T 19/00 | (2011.01) |
| A61B 5/00 | (2006.01) |

(52) U.S. Cl.
CPC ............ *A61B 3/102* (2013.01); *A61B 3/0025* (2013.01); *A61B 3/0058* (2013.01); *A61B 5/0066* (2013.01); *A61B 5/748* (2013.01); *A61B 5/7445* (2013.01); *G06F 19/321* (2013.01); *G06T 15/08* (2013.01); *G06T 19/00* (2013.01); *G06T 19/003* (2013.01); *G06T 2210/41* (2013.01); *G06T 2219/028* (2013.01)

(58) Field of Classification Search
None
See application file for complete search history.

(56) References Cited

U.S. PATENT DOCUMENTS

| | | |
|---|---|---|
| 5,321,501 A | 6/1994 | Swanson et al. |
| 6,266,452 B1 | 7/2001 | McGuire |
| (Continued) | | |

OTHER PUBLICATIONS

Wojtkowski et al., "Ophthalmic Imaging by Spectral Optical Coherence Tomography", American Journal of Ophthalmology, vol. 138, No. 3, Sep. 2004, pp. 412-419.
(Continued)

*Primary Examiner* — Vu Nguyen
(74) *Attorney, Agent, or Firm* — Morrison & Foerster LLP

(57) ABSTRACT

An OCT imaging system user interface is disclosed for efficiently providing relevant image displays to the user. These displays are used during image acquisition to align patients and verify acquisition image quality. During image analysis, these displays indicate positional relationships between displayed data images, automatically display suspicious analysis, automatically display diagnostic data, simultaneously display similar data from multiple visits, improve access to archived data, and provide other improvements for efficient data presentation of relevant information.

8 Claims, 9 Drawing Sheets
(8 of 9 Drawing Sheet(s) Filed in Color)

Related U.S. Application Data

No. 14/245,910, filed on Apr. 4, 2014, now Pat. No. 9,483,866, which is a division of application No. 13/549,370, filed on Jul. 13, 2012, which is a division of application No. 11/978,184, filed on Oct. 26, 2007, now Pat. No. 8,223,143.

(60) Provisional application No. 60/857,451, filed on Nov. 7, 2006, provisional application No. 60/854,872, filed on Oct. 27, 2006.

(56) References Cited

U.S. PATENT DOCUMENTS

| | | |
|---|---|---|
| 6,542,153 B1 | 4/2003 | Liu et al. |
| 6,546,272 B1 | 4/2003 | MacKinnon et al. |
| 6,771,736 B2 | 8/2004 | Sabol et al. |
| 6,934,698 B2 | 8/2005 | Judd et al. |
| 7,015,907 B2 | 3/2006 | Tek et al. |
| 7,020,313 B2 | 3/2006 | Declerck et al. |
| 7,050,615 B2 | 5/2006 | Avinash et al. |
| 7,084,128 B2 | 8/2006 | Yerxa et al. |
| 7,301,644 B2 | 11/2007 | Knighton et al. |
| 7,347,548 B2 | 3/2008 | Huang et al. |
| 7,401,921 B2 | 7/2008 | Baker et al. |
| 7,566,128 B2 | 7/2009 | Tsukada et al. |
| 7,641,338 B2 | 1/2010 | Fukuma et al. |
| 7,668,342 B2 | 2/2010 | Everett et al. |
| 7,768,652 B2 | 8/2010 | Everett |
| 7,782,464 B2 | 8/2010 | Mujat et al. |
| 8,045,176 B2 | 10/2011 | Everett et al. |
| 8,223,143 B2 | 7/2012 | Dastmalchi et al. |
| 8,332,016 B2 | 12/2012 | Stetson |
| 8,894,207 B2 | 11/2014 | Hee et al. |
| 8,931,904 B2 | 1/2015 | Torii et al. |
| 8,944,597 B2 | 2/2015 | Meyer et al. |
| 9,033,510 B2 | 5/2015 | Narasimha-Iyer et al. |
| 9,420,945 B2 | 8/2016 | Coelho et al. |
| 9,483,866 B2 | 11/2016 | Stetson |
| 2003/0164860 A1 | 9/2003 | Shen et al. |
| 2004/0027359 A1 | 2/2004 | Aharon et al. |
| 2004/0161144 A1 | 8/2004 | Barth |
| 2005/0238253 A1 | 10/2005 | Behrenbruch et al. |
| 2006/0030768 A1 | 2/2006 | Ramamurthy et al. |
| 2006/0119858 A1 | 6/2006 | Knighton et al. |
| 2006/0184014 A1 | 8/2006 | Pfeiler |
| 2006/0187462 A1 | 8/2006 | Srinivasan et al. |
| 2007/0025642 A1 | 2/2007 | Buckland et al. |
| 2007/0070295 A1 | 3/2007 | Tsukada et al. |
| 2007/0115481 A1 | 5/2007 | Toth et al. |
| 2007/0216909 A1 | 9/2007 | Everett et al. |
| 2007/0222946 A1 | 9/2007 | Fukuma et al. |
| 2007/0291277 A1 | 12/2007 | Everett et al. |
| 2009/0244485 A1 | 10/2009 | Walsh et al. |
| 2010/0073633 A1 | 3/2010 | Uchida et al. |
| 2010/0079580 A1 | 4/2010 | Waring, IV |
| 2010/0128943 A1 | 5/2010 | Matsue et al. |
| 2011/0109631 A1 | 5/2011 | Kunert et al. |
| 2011/0299034 A1 | 12/2011 | Walsh et al. |
| 2012/0249956 A1 | 10/2012 | Narasimha-Iyer et al. |
| 2013/0181976 A1 | 7/2013 | Dastmalchi et al. |
| 2013/0188132 A1 | 7/2013 | Meyer et al. |
| 2014/0218363 A1 | 8/2014 | Dastmalchi et al. |

OTHER PUBLICATIONS

Ajtony et al., "Relationship between Visual Field Sensitivity and Retinal Nerve Fiber Layer Thickness as Measured by Optical Coherence Tomography", Investigative Ophthalmology & Visual Science, vol. 48, No. 1, Jan. 2007, pp. 258-263.

Bashkansky et al., "Statistics and Reduction of Speckle in Optical Coherence Tomography", Optics Letters, vol. 25, No. 8, Apr. 15, 2000, pp. 545-547.

Bengtsson et al., "A New Generation of Algorithms for Computerized. Threshold Perimetry, SITA", Acta Ophthalmologica Scandinavica, vol. 75, 1997, pp. 368-375.

Budenz et al., "Reproducibility of Retinal Nerve Fiber Thickness Measurements Using the Stratus OCT in Normal and Glaucomatous Eyes", Investigative Ophthalmology & Visual Science, vol. 46, No. 7, Jul. 2005, pp. 2440-2443.

Budenz et al., "Sensitivity and Specificity of the StratusOCT for Perimetric Glaucoma", Ophthalmology, vol. 112, No. 1, Jan. 2005, pp. 3-9.

Carpineto et al., "Custom Measurement of Retinal Nerve Fiber Layer Thickness Using Stratus OCT in Normal Eyes", European Journal of Ophthalmology, vol. 15, No. 3, 2005, pp. 360-366.

Chang et al., "New Developments in Optical Coherence Tomography for Glaucoma", Current Opinion in Ophthalmology, vol. 19, 2008, pp. 127-135.

Choma et al., "Senstivity Advantage of Swept Source and Fourier Domain Optical Coherence Tomography", Optical Express, vol. 11, No. 18, 2003, pp. 2183-2189.

De Boer et al., "Improved Signal-to-Noise Ratio in Spectral-Domain Compared with Time-Domain Optical Coherence Tomography", Optics Letters, vol. 28, No. 21, Nov. 1, 2003, pp. 2067-2069.

El Beltagi et al., "Retinal Nerve Fiber Layer Thickness Measured with Optical Coherence Tomography Is Related to Visual Function in Glaucomatous Eyes", Ophthalmology, vol. 110, No. 11, Nov. 2003, pp. 2185-2191.

Final Office Action received for U.S. Appl. No. 11/978,184, dated Jan. 10, 2012, 23 pages.

Final Office Action received for U.S. Appl. No. 13/549,370, dated Jan. 6, 2014, 14 pages.

Final Office Action received for U.S. Appl. No. 14/199,874, dated Jan. 4, 2016, 9 pages.

Frangi et al., "Model-Based Quantitation of 3-D Magnetic Resonance Angiographic Images", IEEE Transactions on Medical Imaging, vol. 18, No. 10, Oct. 1999, pp. 946-956.

Frangi et al., "Multiscale Vessel Enhancement Filtering", Lecture Notes in Computer Science, vol. 1496, 1998, pp. 130-137.

Gardiner et al., "Evaluation of the Structure-Function Relationship in Glaucoma", Investigative Ophthalmology & Visual Science, vol. 46, No. 10, Oct. 2005, pp. 3712-3717.

Gerig et al., "Nonlinear Anisotropic Filtering of MRI Data", IEEE Transactions on Medical Imaging, vol. 11, No. 2, Jun. 1992, pp. 221-232.

Haeker et al., "Use of Varying Constraints in Optimal 3-D Graph Search for Segmentation of Macular Optical Coherence Tomography Images", MICCAI, vol. 10, Part-1, 2007, pp. 244-251.

Harwerth et al., "Linking Structure and Function in Glaucoma", Progress in Retinal and Eye Research, 2010, pp. 1-23.

Hausler et al., "'Coherence Radar' and 'Spectral Radar'-New Tools for Dermatological Diagnosis", Journal of Biomedical Optics, vol. 3, No. 1, Jan. 1998, pp. 21-31.

Hitzenberger, Christoph K., "Three-Dimensional Imaging of the Human Retina by High-Speed Optical Coherence Tomography", Optics Express, vol. 11, No. 21, pp. 2753-2761.

Hougaard et al., "Glaucoma Detection by Stratus OCT", J Glaucoma, vol. 16, No. 3, May 2007, pp. 302-306.

Huang et al., "Optical Coherence Tomography", Science, vol. 254, Nov. 22, 1991, pp. 1178-1181.

Ishikawa et al., "Macular Segmentation with Optical Coherence Tomography", Investigative Ophthalmology & Visual Science, vol. 46, No. 6, 2005, pp. 2012-2017.

Jiao et al., "Simultaneous Acquisition of Sectional and Fundus Ophthalmic Images with Spectral-Domain Optical Coherence Tomography", Optics Express, vol. 13 No. 2, Jan. 24, 2005, pp. 444-452.

Lee et al., "In vivo Optical Frequency Domain Imaging of Human Retina and Choroid", Optics Express, vol. 14, No. 10, May 15, 2006, pp. 4403-4411.

Leitgeb et al., "Performance of Fourier Domain vs. Time Domain Optical Coherence Tomography", Optics Express vol. 11, No. 8, Apr. 21, 2003, pp. 889-894.

(56) References Cited

OTHER PUBLICATIONS

Leitgeb et al., "Ultrahigh Resolution Fourier Domain Optical Coherence Tomography", Optics Express, vol. 12, No. 10, May 17, 2004, pp. 2156-2165.
Leung et al., "Comparative Study of Retinal Nerve Fiber Layer Measurement by StratusOCT and GDx VCC, II: Structure/Function Regression Analysis in Glaucoma", Investigative Ophthalmology & Visual Science, vol. 46, No. 10, Oct. 2005, pp. 3702-3711.
Maintz et al., "A Survey of Medical Image Registration", Medical Image Analysis, vol. 2, No. 1, 1998, pp. 1-36.
Maurer et al. "A Review of Medical Image Registration", Vanderbilt University Nashville Tennessee 37235, Jan. 28, 1993, pp. 1-49.
Nassif et al., "In vivo Human Retinal Imaging by Ultrahigh-Speed Spectral Domain Optical Coherence Tomography", Optics Letters, vol. 29, No. 5, Mar. 1, 2004, pp. 480-482.
Non Final Office Action received for U.S. Appl. No. 11/978,184 dated Jul. 18 2011, 17 pages.
Non Final Office Action received for U.S. Appl. No. 13/549,370, dated Jul. 2, 2013, 12 pages.
Non Final Office Action received for U.S. Appl. No. 14/199,874, dated Jul. 2, 2015, 10 pages.
Non-Final Office Action received for U.S. Appl. No. 13/740,875, dated Jun. 6, 2014, 11 pages.
Non-Final Office Action received for U.S. Appl. No. 14/245,910 dated Mar. 25 2016, 13 pages.
Non-Final Office Action received for U.S. Appl. No. 15/289,403, dated Dec. 20, 2016, 10 pages.
Notice of Allowance Action received for U.S. Appl. No. 14/245,910 dated Jun. 29, 2016, 11 pages.
Notice of Allowance received for U.S. Appl. No. 13/740,875, dated Oct. 8, 2014, 7 pages.
Notice of Allowance received for U.S. Appl. No. 11/978,184 dated Mar. 20, 2012, 14 pages.
Notice of Allowance received for U.S. Appl. No. 11/978,184 dated May 10, 2012, 4 pages.
Pal et al., "A Review on Image Segmentation Techniques", Pattern Recognition, vol. 26, No. 9, 1993, pp. 1277-1294.
Paunescu et al., "Reproducibility of Nerve Fiber Thickness, Macular Thickness, and Optic Nerve Head Measurements Using StratusOCT", Investigatative Ophthalmology & Visual Science, vol. 45, No. 6, Jun. 2004, pp. 1716-1724.
Perona et al., "Scale-Space and Edge Detection Using Anisotropic Diffusion", IEEE Transaction on Pattern Analysis and Machine Intelligence, vol. 12, No. 7, Jul. 1990, pp. 629-639.

Podoleanu et al., "Combined Multiplanar Optical Coherence Tomography and Confocal Scanning Ophthalmoscopy", J. Biomed Optics, vol. 9, No. 1, 2004, pp. 86-93.
Podoleanu et al., "Transversal and Longitudinal Images from the Retina of the Living Eye using Low Coherence Reflectomety", J Biomed Optics, vol. 3, 1998, pp. 12-20.
Sadda et al., "Errors in retinal thickness measurements obtained by optical coherence tomography" Ophthalmology vol. 113, No. 2, Feb. 2006, pp. 285-293.
Sato et al., "Correlation Between Retinal Nerve Fibre Layer Thickness and Retinal Sensitivity", Acta Ophthalmologica, vol. 86, 2008, pp. 609-613.
Sato et al., "Three-Dimensional Multi-Scale Line Filter for Segmentation and Visualization of Curvilinear Structures in Medical Images", Medical Image Analysis, vol. 2, No. 2, 1998, pp. 143-168.
Schmitt et al., "Speckle in Optical Coherence Tomography", Journal of Biomedical Optics, vol. 4, No. 1, Jan. 1999, pp. 95-105.
Schuman et al., "Reproducibility of Nerve Fiber Layer Thickness Measurements Using Optical Coherence Tomography", Ophthalmology, vol. 103, No. 11, Nov. 1996, pp. 1889-1898.
Sommer et al., "Clinically Detectable Nerve Fiber Atrophy Precedes the Onset of Glaucomatous Field Loss", Arch Ophthalmol., vol. 109, Jan. 1991, pp. 77-83.
Tan et al., "Detection of Macular Ganglion Cell Loss in Glaucoma by Fourier-Domain Optical Coherence Tomography", Ophthalmology, vol. 116, No. 12, Dec. 2009, pp. 2305-2314.e2.
Vermeer et al., "A Model Based Method for Retinal Blood Vessel Detection", Computers in Biology and Medicine, vol. 34, 2004, pp. 209-219.
Wojtkowski et al., "Three-dimensional Retinal Imaging with High-Speed Ultrahigh-Resolution Optical Coherence Tomography", Ophthalmology, vol. 112, Oct. 2005, pp. 1734-1746.
Yanuzzi et al., "Ophthalmic Fundus Imaging: Today and Beyond", American Journal of Opthalmoscopy, vol. 137, No. 3, Mar. 2004, pp. 511-524.
Yu et al., "Speckle Reducing Anisotropic Diffusion", IEEE Transactions on Image Processing, vol. 11, No. 11, Nov. 2002, pp. 1260-1270.
Zana et al., "A Multimodal Registration Algorithm of Eye Fundus Images Using Vessels Detection and Hough Transform", IEEE Transactions on Medical Imaging, vol. 18, No. 5, May 1999, pp. 419-428.
Zawadzki et al., "Adaptation of a Support Vector Machine Algorithm for Segmentation and Visualization of Retinal Structures in Volumetric Optical Coherence Tomography Data Sets", Journal of Biomedical Optics, vol. 12, No. 4, Jul./Aug. 2007, pp. 041206-1-041206-8.

USER INTERFACE FOR EFFICIENTLY DISPLAYING RELEVANT OCT IMAGING DATA

PRIORITY

This application is a continuation of U.S. application Ser. No. 15/289,403, filed Oct. 10, 2016, which is a continuation of U.S. application Ser. No. 14/245,910, filed on Apr. 4, 2014, now U.S. Pat. No. 9,483,866, which is a divisional of U.S. application Ser. No. 13/549,370, filed Jul. 13, 2012, which is a divisional of U.S. application Ser. No. 11/978,184, filed Oct. 26, 2007, now U.S. Pat. No. 8,223,143, all of which are incorporated by reference. This application claims the benefit of the filing date under 35 U.S.C. § 119(e) of Provisional U.S. Patent Application Ser. No. 60/854,872, filed on Oct. 27, 2006, and Provisional U.S. Patent Application Ser. No. 60/857,451, filed on Nov. 7, 2006, which are hereby incorporated by reference in their entirety.

ACKNOWLEDGEMENT OF GOVERNMENT SUPPORT

Portions of this disclosure were developed with Government support under Grant No. 6 R44EY014099-0, awarded by the National Institute of Health. The Government may have certain rights in the claimed inventions.

TECHNICAL FIELD OF THE INVENTION

The present invention relates to optical medical imaging, and in particular to systems that are adapted to perform Optical Coherence Tomography ("OCT") for use in diagnosis and monitoring of tissue health.

BACKGROUND OF THE INVENTION

Optical Coherence Tomography (OCT) is a technology for performing high-resolution real time optical imaging in situ. OCT herein refers to any of the transverse scanning extensions of one-dimensional optical coherence detection techniques generally derived from optical coherence domain reflectometry (OCDR) or optical frequency domain reflectometry (OFDR). OCT is an optical measurement and imaging technique using low-coherent light from a broadband source or a tunable laser to create interference signals across the tunable wavelength range of the laser to illuminate both a reference path and a sample path. The superposition of backscatter reflection from the sample path and the optical signal from the reference path creates an interference pattern. The interference pattern contains information about the scattering amplitude as well as the location of the scattering sites in the sample. The longitudinal range within the sample is obtained by using time domain or frequency domain optical coherence techniques. This depth profile is commonly called an "A-scan". Cross-sectional images are synthesized by laterally scanning the sample beam over a series of adjacent A-scans, 2-D and 3-D image scanning. OCT provides a mechanism for micrometer resolution measurements.

Evaluation of biological materials using OCT was first disclosed in the early 1990's (see U.S. Pat. No. 5,321,501). More recently it has been demonstrated that frequency domain OCT has significant advantages in speed and signal to noise ratio as compared to time domain OCT (Leitgeb, R. A., et al., Optics Express 11:889-894; de Boer, J. F. et al., Optics Letters 28: 2067-2069; Choma, M. A., and M. V. Sarunic, Optics Express 11: 2183-2189). In Spectral Domain OCT (SD-OCT), sometimes also referred to as Frequency Domain OCT (FD-OCT), and also sometimes also referred to as Spectral Radar (*Optics letters*, Vol. 21, No. 14 (1996) 1087-1089), the measurement is achieved by examining the spectral content of the interference pattern out of the interferometer.

Improvements in imaging displays frequently accompany improvements in data acquisition methods and devices. For example, development of higher resolution imaging devices creates a need or motivation for higher resolution imaging displays; faster 2-D data acquisition increases the need for high speed data transmission and storage and motivates improvements in 3-D display applications; improvements in the signal to noise ratio in acquired data stimulates new uses and displays for that information.

Large medical imaging data sets, such as those acquired during volumetric imaging, present difficulties in displaying relevant information to operators/users. Medical practitioners need to obtain relevant information quickly in a format that can be efficiently processed. A traditional approach to displaying 3-D volumes is multi-planar reconstruction, which simultaneously displays images from different viewing angles. The user then "scrolls" through the volume looking for relevant images. An alternative approach utilizes modern computational power to identify features of interest and present these to the user through volume rendering. Many times, however, an expert user benefits from observing individual slices of the image data directly. However, selection of these images can be time-consuming and there is a need to improve the means for accessing relevant slices. Herein, a volume slice will generally refer to planar data extracted from a volume, while B-scan will refer to a planar section of the volume that was acquired sequentially. In this sense, a B-scan is a slice, while a slice may be a B-scan. However, the terms are often used interchangeably in the literature and the distinction is often not relevant, since a slice could have been a B-scan under an alternative scanning sequence.

Increased longevity within the population increases the likelihood of age related conditions, such as macular degeneration and glaucoma. Loss of vision, whether partial or complete, dramatically affects quality of life. Whether vision loss is due to changes in the anterior, posterior, or interior of the eye, monitoring change can be crucial to modern patient management.

Change analysis is the detection of change in the condition of a patient over time. Change analysis has great potential for improving patient care in areas such as diagnostic monitoring, intervention planning, and progress monitoring. Modern computing and digital imaging make it possible to store and retrieve large quantities of patient imaging data. Taking diagnostic advantage of these large quantities of data requires improvements in access and management of diagnostic combinations of imaging data within an analysis package. For many diseases, there remains an active debate over what should be measured and tracked over time to track and/or predict disease progression.

Glaucoma is a term generally referring to the collection of diseases related to loss of retinal ganglion cell function. Glaucoma is a slowly progressive disease that, unless treated (and sometimes even when treated), can result in blindness. While raised intraocular pressure (TOP) is a symptom within a sub-family of these diseases, one patient's damaging TOP may well be completely tolerated by another patient with no discernable visual affects. (See U.S. Pat. No. 7,084,128, Yerxa, et al., "Method for reducing intraocular pressure") Glaucoma Progression Analysis (GPA) software developed with Carl Zeiss Meditec by Dr. Anders Heijl represents the current state of Progression Analysis for Glaucoma. This software monitors visual field loss progression by examining the patient's response to visual field stimuli over time.

Macular degeneration describes a disease or family of diseases that are characterized by a progressive loss of central vision. Vision loss is generally associated with abnormalities in the choroid, Bruch's membrane, the neural retina and/or the retinal pigment epithelium. Destruction of a vascular function within the choroid depletes nourishment to retinal layers and damages overall visual function. Since such destruction is, at present, not generally repairable, recognition of the vascular failure frequently comes too late to be of any real value to the patient. Retinitis and retinopathy are retinal degradations that may progress into total loss of vision. Tracking the change (progression or regression) of eye function both prior to and post treatment improves diagnosis and treatment. Tracking changes over time improves the timing of intervention and enables more effective patient management.

In light of the above, there is a need in the art for an efficient method and apparatus designed to provide to the user relevant image displays and analysis of the large data sets associated with volume OCT imaging. There is a need to display the relevant images needed to track changes over time. The present invention meets the need to provide relevant image displays to the user, overcoming past obstacles by improved data presentation.

SUMMARY

The scope of the present invention is defined by the claims that follow. Nothing in this section should be taken as a limitation on those claims.

In accordance with one aspect of the present invention, the imaging system displays a small sample of image data in real time prior to volume data acquisition enabling the user to align the imaging system before acquiring a full volume image.

In another aspect of the present invention, the imaging system processes a small sample of image data and automatically aligns the system before acquiring a full volume image.

In another aspect of the present invention, on a patient's second or later exam, the medical provider can retrieve imaging data from one or more previous exams, register imaging data across multiple visits and display image data from two or more exam visits at the same time.

In another aspect of the present invention, navigation through one set of image data automatically navigates and displays equivalent image data from another exam.

In yet another aspect of the present invention, image movies played from one exam are synchronized and registered to display the corresponding region in another exam so that the change in image data can be readily ascertained. In one instantiation of this aspect of the present invention, the time scale for navigating through the image movie is non-linear.

In yet another aspect of the present invention, the imaging system uses a small sample of image data to align the system automatically before acquiring a full volume image.

In yet another aspect of the present invention, user navigation through one image dataset is registered with another exam so that displayed analysis images from both exams display corresponding data.

In yet another aspect of the present invention, user modification of a boundary in a single image is propagated throughout a sequence of images.

In yet another aspect of the present invention, a summary image is displayed alongside of an OCT image slice and the location of the OCT image slice within the volume is displayed in the summary image. Alternatively, an analysis image can be derived from the OCT volume data and displayed, overlaid over the summary image.

In yet another aspect of the present invention, thumbnails are combined to form a combination thumbnail, which can be used to identify and/or retrieve the exam.

In yet another aspect of the present invention, at least one image of the display contains a confidence map. The confidence map is indicative of the confidence in the segmentation performed either on slice or volume data.

In yet a further aspect of the present invention, software automatically identifies the most relevant images, such as specific B-scans or arbitrary slices, and displays them to the user as an image.

The analysis of the change over time of physical attributes is a well-known diagnostic tool. Herein is provided a method and apparatus providing a user interface for efficiently displaying relevant OCT imaging data.

BRIEF DESCRIPTION OF THE DRAWING

The patent or application file contains at least one drawing executed in color. Copies of this patent or patent application publication with color drawing(s) will be provided by the Office upon request and payment of the necessary fee.

DETAILED DESCRIPTION

The present invention is a User Interface (UI) efficiently providing the user with relevant OCT image displays. In one instance, the UI simultaneously displays images of the same region acquired during examinations performed at separate visits. Such displays enable the service provider to monitor changes in the patient's condition over time. The User Interface disclosed is useful for acquiring data, reviewing acquired data, simultaneously viewing multiple images, and manipulating analysis displays. The User Interface provides access to analysis applications that identify regions of interest, reduce the data, and display relevant information in an efficient manner. The User Interface uses image overlays to increase information density in a display area with minimal impact to the underlying display. Overlays help the user find, understand the location of, and visualize relevant data. Image thumbnails and composite image thumbnails are used to readily recognize (and optionally retrieve) exams from which they were derived. This User Interface has been implemented in conjunction with an imaging system described in co-pending U.S. patent Ser. No. 11/820,773, filed Jun. 20, 2007, (published as US 2007/0291277) incorporated herein by reference. However, said User Interface can, for many of its functions, perform equally well on a stand-alone platform with access to OCT data files.

Patient Alignment

Figure 1:
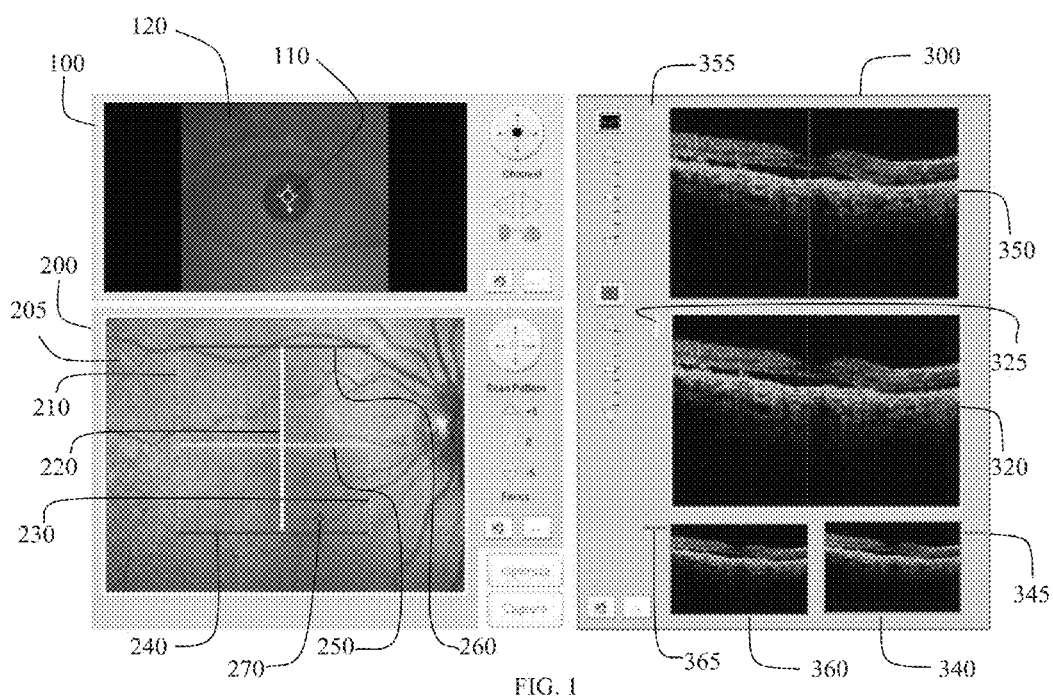
FIG. 1 illustrates a user interface for aligning tissue for data acquisition.

Optimal patient imaging requires proper patient alignment. The User Interface can only function to help proper patient alignment when running on the image collection system. FIG. 1 illustrates a user interface display for aligning patients. For retinal exams, proper alignment is achieved when the target region of the retina is centered and focused, the retinal arc is centered in the central horizontal and vertical slices, and the maximal extent of the retina is visible within the volume cube. Ostensibly, there are three steps to patient alignment: aligning the patient's head in front of the ocular lens of the instrument so that the working distance is correct (that is, the imaging system is aligned properly with the pupil), aligning the optics to correct for refractive error, and aligning the OCT imager to image at the correct depth. A fourth step, polarization compensation between reference and source arms in the OCT imager to improve image quality, can also be performed, but it does not require changing the focal point of any portion of the imaging system with respect to the patient.

The first step in proper patient alignment for the imaging system of U.S. patent Ser. No. 11/820,773 is aligning the patient's head in front of the ocular lens so that the working distance is correct. In FIG. 1, the upper left viewport 100 displays an Iris Viewer image 120. The Iris Viewer image is a high contrast image of the iris surrounding a central dark pupil. This image is used for aligning the patient working distance. Icon 110 overlays the Iris Viewer image showing the entry point of the scan beam and is used for aligning the pivot point of the scan beam on the subject's pupil. In the illustrated embodiment, icon 110 is in the form of a crosshair target. The Iris Viewer described in U.S. patent Ser. No. 11/820,773 and motorized chin rest described in co-pending U.S. patent Ser. No. 10/843,767, filed May 12, 2004, Publication No. 2005/0254009, incorporated herein by reference, are integrated; the motorized chin rest responds to User Interface input from the Iris Viewer viewport. User Interface input provided by selecting a point in the Iris Viewer (e.g. mouse click) instructs the motorized chin rest to move the patient in the X-Y plane so that the entry point of the scan beam 110 corresponds to the point selected in the image. In order to focus the iris image, user input commands the User Interface CPU to instruct the motorized chin rest to move the patient along the Z-axis. Once the iris and pupil are in focus, the correct working distance between the instrument and the patient's eye is set. Construction of the instrument is such that the scan beam pivot point is approximately at the focal plane of the iris viewer. Thus, setting the correct working distance puts the pivot point of the scan beam in the plane of the patient's iris. It would also be possible to have a system wherein the housing that contains the optical element moves and the patient is stationary. In that case, the alignment would be performed by moving the housing.

The second step in proper patient alignment for this system is aligning the optics to correct for refractive error. In FIG. 1, the lower left viewport 200 displays a summary image 205, nominally a real time fundus image from a fundus camera or a line-scanning ophthalmoscope (LSO) or other fundus imager. The system of U.S. patent Ser. No. 11/820,773 achieves its best correction for refractive error when the retinal image of the fundus imager is optimally focused. In order to focus the retinal image, the user provides input commands to the User Interface CPU to instruct the motorized chin rest to move the patient and ocular lens in combination along the Z-axis. In this case, the ocular lens is also moved so that the distance between the ocular lens and the patient remain fixed, thereby retaining the Iris viewer focus and preserving the pivot point alignment.

The third step in proper patient alignment is aligning the OCT imager to image at the correct depth. In FIG. 1, the lower left viewport 200 displays a summary image 205, nominally a real time fundus image or an integrated OCT en-face image. During cube scan alignment, the system of U.S. patent Ser. No. 11/820,773 displays line segment overlays 210, 230, and dashed white segments not seen below the lines 240 and 260 in the summary image outlining the extent of the acquisition volume (the volume to be acquired). Scan location icons 220, 240, 250, and 260 overlay the fundus image in the summary window indicating the location of four alignment B-scans. In viewport 300, images 320 and 350 show scans from locations 220 and 250, respectively. These are the central vertical and horizontal B-scans, respectively. Images 340 and 360 are reduced size images of the bottom and top B-scans of the acquisition volume, taken from locations 240 and 260, respectively. The user provides input commands to the User Interface CPU to instruct the OCT imager to set the OCT image delay line so that the retinal image in displays 320, 340, 350, and 360 is optimally located.

Optionally, a fundus image or integrated OCT en-face image from a previous examination can be overlaid on the live fundus image 205 in a semi-transparent manner. Aligning the previous OCT en-face image and the live fundus image ensures that the volume within the region bounded by 210, 230, 240, and 260 will image the same region as was acquired during the previous exam. When a previous fundus image is registered to the OCT en-face from the same exam, aligning the previous fundus image with the live fundus image enables the acquisition of the same (or nearly the same) OCT volume region as was acquired during the previous exam. This optional step is preferentially performed after refractive error alignment and before completion of the step setting the OCT imager delay line for systems using a spectral domain OCT imager.

The term en-face appears in a variety of forms in the literature. Various authors use at least three forms: en face, en face, and en-face. All forms are equivalent and, in the field of ophthalmology, an OCT en-face image is an image extracted from a 3D OCT volume by integrating the OCT signal along a viewpoint, generally over a range of depths, as described in Knighton, et al., 20060119858.

It is important to control the position of the patient's eye. Eye movement causes the OCT imager to view different regions of the eye. Moving the eye can be useful when performing the optional alignment to a previous exam described above. Moving the eye can also be used to achieve a particular imaging path (to avoid a particular part of the cornea, which might be damaged, or to avoid a cataract in the crystalline lens.) The User Interface (UI) provides access to control an image fixation subsystem. The patient fixates on a target projected by the fixation subsystem. Through the fixation subsystem, the UI controls the position of the eye by controlling the location of the fixation target image. The line-scanning ophthalmoscope (LSO) fundus imager and fixation subsystem described in U.S. patent Ser. No. 11/820, 773 are integrated; the fixation target 270 of the fixation subsystem responds to User Interface input from the summary image (LSO) viewport. During OCT image capture, the patient focuses on a fixation target, helping to reduce or prevent eye movement. The UI allows the user to select a point in the summary image (e.g. mouse click) and the UI CPU instructs the fixation subsystem to move the fixation target in the X-Y plane so that as long as the patient follows the fixation target, the selected point becomes the center of the fundus image. Thus, the center of the acquisition volume (in the X-Y projection plane) becomes the selected point in the fundus image.

During OCT image depth alignment, Viewport 300 of FIG. 1 displays four alignment B-scans of the acquisition volume. Through these four images, the user can verify proper patient alignment. Clearly, those versed in the art will understand that other images can be used for this purpose. For example, images obtained from locations 210 and 230 can replace images 340 and 360, obtained from locations 240 and 260. Alternatively, two B-scans diagonally intersecting the image cube are theoretically sufficient, without any additional border images. However, the images shown in Viewport 300 are sufficient and readily understood.

The description provided here for optimally aligning OCT depth range for OCT volume capture describes OCT volume imaging of the fovea. One skilled in the art can readily generalize to imaging the optic nerve or other imaging applications (including the imaging the cornea). For acquiring volume cube scans using the UI of FIG. 1, after the scanning beam entry point is aligned (steps 1 and 2 above), proper OCT depth range alignment can be attained by locating five (5) points: the extremal point of the retina within the cube scan and the four points of the retina at the intersections of the planes bordering the cube scan (four corner points). The extremal point of the retina is the retinal point furthest from the imaging device. The four corner points of the retina are the four points of the retina closest to the imaging device along the four lines formed at the intersections of planes bounding the sides of the cube. The central point of the retina is the retinal point at the center of the X-Y projection of the volume. For proper alignment, the extremal point should be at or near the central point and the four corner points of the retina should be within the scan volume. The UI of this invention displays regions of the volume cube in neighborhoods of the 5 points and accepts user input to direct moving the 5 points to where they should be. Aligning these 5 points to their optimal locations is sufficient to align the OCT depth for proper patient imaging.

Images 320 and 350 are the central vertical and horizontal B-scans of the acquisition volume, respectively. The retinal curvature within these images is determined by the degree of myopia of the subject eye. For foveal imaging, the scan beam entry point is properly located when the shape of the retina in images 320 and 350 is approximately symmetric about the fovea and the fovea is located approximately one-half way across each image. If the retina is not symmetric about the fovea, the user adjusts the entry location 110 through the Iris Viewer viewport interface. If the fovea is located approximately one-half way across each image, the fovea is properly centered in the X-Y plane. If the fovea is not properly centered in the X-Y plane, the user adjusts the center of the acquisition volume within the summary viewport. The entry angle centered on the fovea is adjusted by moving the fixation target to relocate the eye in combination with moving the entry point to re-center the fovea.

The volume alignment process ensures that the tissue of interest will be within the volume scanned. The UI displays B-scans 350, 320, 340, and 360 so that, if the retina is within the depth range of each of these B-scans, it is with high probability within the depth range of the entire volume. (Mathematically, for a retina with smooth anterior and posterior surfaces and without inflection or saddle points, the retina will be within the volume range with probability 1.) We first ensure that the point of the retinal image that is furthest from the imaging device will be within the volume scanned. After the previous alignment steps are properly performed, this point will lie near the intersection of the line normal to the central horizontal scan 350 through the point of the retinal image that is furthest from the imaging device in scan 350 and the line normal to the central vertical scan 320 through the point of the retinal image that is furthest from the imaging device in scan 320. When the imaging system is properly aligned, this point is on (or nearly on) the line segment at the intersection of scans 320 and 350. Because of the continuity and curvature of the retina, the extremal point is within the volume scan if the extrema of the retinal arcs within scans 320 and 350 are each within their respective images (or sufficiently within their respective images when compared to the curvature of the retina and their offset from the extremal point.) Placement of the extremal point within the image volume ensures that the image of the retina does not "drop out" of the bottom of the volume image.

The user ensures that the retinal image does not "pop through" the top of the volume cube by checking images 340 and 360. If the retinal image lies within each edge (A-line) where the sides of the cube meet, then the corner points of the retina lie within acquisition volume and the retinal image will be within the volume cube. Thus, for every horizontal and vertical slice of the volume, the retinal image will remain within the slice. That is, if the retinal image is visible within each of the edges of the cube, then the OCT depth range is correctly set and the OCT image cube range is properly aligned. The advantage of a User Interface displaying images as in viewport 300 is that a user viewing the four images can quickly and easily determine if the acquisition volume is aligned for retinal image acquisition. That is, if the upper and lower edges of the retina are visible across all four images displayed and the extremal point is visible within the images, then the acquisition volume is aligned for capturing the retinal volume image. In other words, if the Retinal Nerve Fiber Layer (RNFL) and Retinal Pigment Epithelium (RPE) are visible across all four images displayed, the acquisition volume is aligned.

In SD-OCT systems that have not otherwise eliminated the mirror image in the spectral detection path, one needs to ensure that it is the image of the retina and not the mirror image of the retina that is visible within the four edge A-lines. For ease of use and consistency in the display, two tomograms from opposite sides of the volume cube are displayed, rather than simply the four edge A-lines of a cube scan. Theoretically, the four edge A-lines (the first and last lines of the two tomograms from opposite sides of the cube) contain enough information to determine the appropriate SD-OCT depth range. However, displaying the two tomograms from opposite sides of the cube simplifies both the display and the user's ability to understand the situation. In FIG. 1, images 340 and 360 enable the user to ensure that the retina will be within the acquisition volume. Additionally, any mirror image will appear folded in the tomogram. Image folding at the top of the slice informs the user that the OCT range is set too deep and that they should adjust the OCT engine to image more shallowly. These tomograms contain the information of the A-lines, which is displayed at the ends of the tomograms. Alternatively, tomograms from locations identified by 210 and 230 could be used instead of the tomograms 340 and 360 because the information contained in the four A-lines needed is also contained within those tomograms. Thus, the User Interface notifies the user if image folding has occurred and enables them to adjust the OCT range to correct the alignment.

Since display space is limited, one UI goal is to minimize the number of images needed for alignment. However, since patient alignment and imaging is the ultimate goal, different displays that make alignment easier, whether by making training easier, by making volume manipulation easier, or by any other means, can be added to the final UI arrangement. The UI of record displays the critical image locations and provide a means to relocate the acquired image volume to properly position the critical image locations within the volume.

Proper alignment requires the user to associate information contained within the various images in each of the three viewports of FIG. 1. The UI simplifies this association by providing slice locators to identify the location within the fundus image of Viewport 200 of the B-scans presented in Viewport 300. The color (yellow) of ID icon 355 and slice locator 250 shows the correspondence between B-scan 350 of Viewport 300 and its location (indicated by line segment 250) within the fundus image of Viewport 200. The ID icon 355 can contain additional slice information, such as the direction of the scan. In this instance, the horizontal yellow bar in the icon identifies image 350 as a horizontal B-scan. Slice 320 is the vertical B-scan from location 220. The color (white) of ID icon 325 and slice locator 220 shows the correspondence between B-scan 320 and its location (indicated by line segment 220.) The correspondence between slices 340 and 360 and their locations in the fundus image (indicated by segments 240 and 260) is indicated by the color (blue) of ID Icon 345 matching the color of slice locator 240 and the color (magenta) of ID Icon 365 matching the color of slice locator 260. The UI uses color in slice locators and ID Icons to simplify user association of images to location. Alternatively or in addition, the UI may use the same color to highlight the border of the slice display.

Finally, the User Interface provides a manual control (not shown in FIG. 1) for polarization compensation between reference and source arms in the OCT imager. Theoretically, this control would control the three polarization paddles necessary for complete compensation of polarization differences between the reference and source arms. In the systems disclosed in U.S. patent Ser. No. 11/820,773 a single polarization paddle is used to simplify the interface and approximately compensate for polarization differences. In this design, a single slider, knob or similar interface is used to move the paddle while the user views the image, looking for the position of the control that maximizes the signal content of the retinal image.

In FIG. 1, the fundus image 205 is an LSO image. The real time fundus image can be from any fundus imager, such as a fundus camera, a scanning laser ophthalmoscope (SLO), or a line scanning laser ophthalmoscope (LSLO), or a line-scanning ophthalmoscope (LSO). Any confocal fundus image is advantageous over any non-confocal fundus imager, like a fundus camera, since the confocal image eliminates or reduces glare and background information away from the focal plane, creates sharply defined images and can be simultaneously acquired with the OCT volume scan when separate wavelengths are used. Confocal imaging produces improved vessel imaging over traditional fundus cameras. Simultaneous imaging is preferred because of shortened exam duration and higher correlation between images. LSO images are acquired even faster than SLO images because of the simultaneous imaging of a line. LSO imaging differs from LSLO imaging largely in that the laser of an LSLO imager is replaced by a In the system described in U.S. patent Ser. No. 11/820, 773, OCT volume scans are commonly called cube scans. However, not all edges are necessarily the same length. In fact, the opposite sides are not necessarily parallel, nor are the top and bottom necessarily flat, so these volumes are not, strictly speaking, even cuboid. The volume may more properly be called a regular 4-sided truncated spherical pyramid. Regardless, the term "cube" is generally used to indicate this nearly cuboid volume with nearly parallel sides and almost planar top and bottom. Clearly, other volumes would suffice as well, such as nearly right regular n-gons or nearly regular truncated n-sided pyramids.

Automatic Patient Alignment

Optionally, prior to volume acquisition, the OCT system can automatically align the retina within the volume scan. To accomplish this, the User Interface CPU causes the system to acquire a limited number of B-scans, performs image processing on the B-scans, determines the location where the retina would appear within the volume scan if the volume scan were performed under this configuration, and re-aligns the system for proper retinal imaging, if needed, before acquiring the volume scan. The alignment steps are the same as for manual alignment. The system first aligns the subject's pupil with the scan beam. That is, the system sets the proper working distance and initial entry point. The patient sits and rests her head in the motorized head support apparatus. The Iris Viewer captures an image, like 120 in FIG. 1, and passes it to the host CPU, which identifies the pupil or iris. The Iris Viewer repeatedly captures iris images, passing them to the host CPU. The CPU determines from the images where the initial X-Y alignment should be and then commands the motorized head support to position the patient for the scan beam to pass through computed point on the pupil. Initial X-Y alignment can be determined by applying standard image processing techniques, such as edge detection. For example, the pupil edge can be detected by thresholding the image of iris image to find the pupil boundary. The CPU also estimates the working distance (the distance between the ocular lens and the pupil or iris) based on the sharpness of focus of the iris and/or pupil. The CPU commands the motorized head support to move the patient's head in the Z direction to set the proper working distance. This is a well-known auto-focus problem. One means of focusing is to move the patient's head repeatedly, analyzing iris images at multiple locations until an optimal focus is achieved. In alternate system designs, the working distance can be set by moving the ocular lens instead of the patient. For the imaging system of U.S. patent Ser. No. 11/820,773, this working distance alignment sets the pivot point of the scan beam substantially in the plane of the patient's iris.

After the working distance is set, the system automatically aligns the optics to correct for refractive error. In one instantiation, the system will automatically acquire a retinal fundus image using a fundus imager such as a Line Scanning Ophthalmoscope (LSO). The host CPU processes the image data to determine sharpness of focus of the retinal image. Again, this poses a well-known auto-focus problem. Alternatively, the system may automatically acquire a B-scan using the OCT imager. The host CPU processes the B-scan image data to determine relative strength of the OCT signal. The host CPU commands the motorized head support to move the patient's head and the system's ocular lens module in combination in the Z direction to focus the fundus imaging system to accommodate the refractive error of the eye. The LSO and OCT systems are designed so that, when the LSO fundus image of the retina is in focus, the OCT imager will produce a sharp retinal image in each B-scan. Because the LSO and OCT systems are co-aligned, the optics correction for refractive error can be performed automatically using either B-scan signal strength or fundus image sharpness. The refractive error correction adjustment preserves the pivot point alignment by moving the head and system ocular module as a unit. At this point, the working distance and refractive error correction are set. For improved focus, the refractive error correction step may be repeated after setting the OCT depth range as described below.

The final positional alignment is automatically set to align the OCT imager to image at the correct depth. One means to accomplish OCT range alignment is for the system to acquire central horizontal and vertical B-scans like 350 and 320 displayed in FIG. 1. (Central horizontal and vertical B-scans are B-scans essentially slicing across center of the OCT volume, either horizontally or vertically, respectively.) For retinal imaging of the fovea, the host CPU can process these images to locate the fovea. Segmentation of the retinal image identifies the retinal fovea by searching for the foveal pit. The fovea can also be identified by pattern recognition techniques, or by other image processing techniques. If the segmentation indicates that the Retinal Pigment Epithelium (RPE) near the fovea lies below the volume acquisition region, then the host CPU commands the OCT depth delay to accommodate imaging at a deeper depth. The host CPU determines the offset needed to center the foveal pit within a volume so that it is centered in the central horizontal and vertical B-scans. The host CPU then commands the Fixation Target subsystem to move the fixation target so that the patient's eye is redirected so that in the new acquisition volume, the central horizontal and vertical B-scans have the foveal pit centrally located. The foveal pit has been identified and centered using only a few B-scans and without a full volume acquisition.

The host CPU commands the Fixation Target subsystem directly. The patient fixates on the fixation target. The fixation target is a fiducial mark generated at a visible wavelength. The fixation target is focused into the eye at a location calculated to cause the patient to orient their eye in a specified direction. When the host CPU moves the fixation target, the patient rotates their eye to follow the fixation target. The pupil rotates with the eye, changing the center location of the pupil. The host CPU commands the motorized chinrest to move sideways to compensate for pupil motion. Thus, the host CPU determines the offset needed, computes the fixation target location needed to sufficiently cause the eye to move to achieve this offset, causes the fixation target to move with the eye following and adjusts the chinrest so that the entry point within the pupil remains optimal.

The host CPU adjusted the OCT range alignment so that the retinal image does not extrude through the bottom of the volume; i.e., the point on the Retinal Pigment Epithelium (RPE) furthest from the imaging device is within the volume scan. The point on the RPE furthest from the imaging device should be directly below the foveal pit in the most recently acquired central horizontal and vertical B-scans. This is the extremal point of the RPE. If the extremal point of the RPE does not intersect the bottom of either B-scan, the margin available to keep the extremal point in the volume is stored. Setting the OCT range so that the extremal point is just above the volume floor ensures that as much of the retina as possible will be within the imaging volume. However, because of edge effects, placing the preferred imaging region centrally within the image volume is advantageous. For this reason, it is also useful to find the retinal points within the volume to be imaged that are closest to the imager.

In order to determine if these retinal points closest to the imager are within the volume to be acquired, two additional B-scans along the boundary of the acquisition volume are acquired. These two scans contain the edges of the acquisition volume, preferably B-scans from opposite sides of the cube like 340 and 360 in FIG. 1. The upper boundary of the retina, the inner limiting membrane (ILM), is segmented in these images. If the ILM extrudes through the top of either B-scan, measurements are performed on the segmented retinal images to estimate the extent to which the retinal image extrudes through the top of the volume. This estimate can be easily performed using a parabolic fit to the ILM within the B-scan. Data indicating the available margin for top adjustment are compared with data indicating the available margin for depth adjustment and a final adjustment is made. The system is automatically aligned for volume acquisition and the volume acquired. In this way, automatic depth adjustment can compensate for variations in the length of the human eye without user intervention. Optionally, once the CPU determines the location of the fovea, it can command the motorized head support to move the patient in the XY plane, moving the entrance location of the scan beam in the patient's pupil to partially level the appearance of the retina in B-scans 320 and 350. This is most useful when the ILM or RPE do not appear symmetric within the limited alignment B-scans.

System volume scan alignment can be automatically optimized even if it is not possible to adjust the system so that the retinal image is fully within the volume scan. The system automatically optimizes scan alignment based on a priori defined imaging preferences. For example, centering the retina within the volume is one optimization criteria. Maintaining image quality of the retinal point furthest from the imaging device is another. In general, the system can automatically adjust image alignment of any tissue of interest, provided the tissue can be identified and a metric applied to the measure of how well the tissue is aligned.

SD-OCT systems that have not otherwise eliminated the mirror image in the spectral detection path can automatically choose the portion of the image that moves consistently with the depth adjustment and reject the mirror image that moves in the opposite direction to the depth adjustment. Because of this, automatic depth adjustment can be used to discriminate between the SD-OCT image and its mirror. Alternatively, chromatic dispersion mismatch can be used separately or in conjunction with depth adjustment to determine which half of the SD-OCT output is the image and which half is the reflection. While the image and the mirror image have the same integrated intensity (when integrated over linear intensities), the true image is sharper and has greater peak intensities. Any measure of the center of the image that weights higher intensity points more than linearly in intensity, will be biased toward the true image. The centroid along depth Z of the square of the intensity in the B-scan is one example measure of the depth position of the retina.

Automatic polarization compensation between reference and source arms in the OCT imager may optionally be automatically performed in conjunction with or after aligning the optics for refractive error correction. In the systems with a single polarization paddle, a simple technique comprised of setting the paddle and examining the resultant image signal content can rapidly scan through multiple paddle settings to maximize the signal content of the retinal image.

Image Acquisition

Once the imaging system is aligned, the OCT volume is acquired. During acquisition, the User Interface removes the alignment overlay and replaces it with a live display of the OCT fundus image. An OCT fundus (or en-face) image is an image created from OCT data by integrating over depth. For performance advantageous, dedicated hardware or firmware in the data acquisition path computes the live display of the OCT fundus, accumulating the signal across depth cells of the A-line as the A-line is acquired. Using this dedicated hardware approach, the B-scan image and the associated line of the OCT en-face image are available for display at the same time, with minimal delay following optical illumination. The live B-scan can replace any one of the alignment B-scan images, preferably in the largest image display window available. The User Interface displays live B-scan in one Viewport and OCT en-face overlaying the LSO fundus display in another Viewport provides the user with real-time information for quality control of the OCT volume acquisition. This UI also provides the user with rapid feedback on the status of the volume acquisition. Since it is common for the user to ask the patient to hold still during the volume capture, it is reassuring when the user has a visual queue showing the exam completion status. The user can assess imaging artifacts in real-time and can initiate re-acquisition quickly and easily with a single command. On completions of volume acquisition, the UI automatically displays a movie of the OCT acquisition B-scans. The speed of the movie playback is variable. Alternatively, a playback mode where the B-scans are displayed quickly for the first and last scans captured and more slowly for the central B-scans allows the user to quickly skim the edge volume information and more carefully examine the B-scans near the center of the volume. A single command can initiate image volume archival.

During acquisition, it is advantageous to acquire not only the OCT volume, but also, for a portion of the volume, to acquire one or more high-definition B-scans. High-definition B-scans are scans of higher resolution than other B-scans within the volume, either by reducing the A-lines spacing within a B-scan or by reducing the B-scan spacing within the volume. Time and data storage constraints limit the number of high-definition scans within the volume. It is advantageous for the central horizontal and vertical B-scans of the volume acquisition to be high-resolution.

Real time high frame rate imaging of the fundus enables the operator to observe in real-time the relative position of the scan area to the fundus. This real-time capability allows the operator to position the scan pattern/area over the area of interest even in the presence of frequent eye movements.

Maximum Intensity Projection

One analysis application or tool for analyzing OCT volumes is the Maximum Intensity Projection (MIP). MIP is a volume rendering technique used to extract high intensity structure from volume data. Live OCT MIP displays provide the user with another tool for viewing the quality of the OCT volume acquisition. Once the imaging region is aligned and volume acquisition begins, the User Interface replaces the alignment displays with a live display of the OCT en-face and one or more Maximum Intensity Projection (MIP) display. For the standard MIP display, at any time during acquisition, the current MIP scan is a pixel-by-pixel maximum of the previously acquired B-scans. That is, for the first B-scan of the volume scan, the MIP scan is the same as the B-scan. Thereafter, when the system acquires the N+1$^{st}$ B-scan of the volume, the N+1$^{st}$ MIP scan is the pixel-by-pixel maximum of the pixel value in the N+1$^{st}$ B-scan and the pixel value of the N-th MIP scan. Mathematically, $$M_{ij}^{N+1}=\max(M_{ij}^N,B_{ij}^{N+1})$$

where $B_{ij}^N$ is the value of the pixel at coordinates (i,j) of the N-th B-scan and $M_{ij}^N$ is the value of the pixel at coordinates (i,j) of the N-th Maximum Intensity Projection scan. Initially, $M_{ij}^1=B_{ij}^1$. The MIP display clearly indicates retinal movement out of the acquisition volume. This display provides a rapid quality check of the acquired volume for most eye motion, providing the user with early notification of one of the most common causes of volume scan failure.

In general, an MIP is a projection of parallel rays through a 3D volume onto a plane perpendicular to the rays. The viewpoint is the direction of the parallel rays. The value at a point in the projection plane is the maximum of the values of the 3D volume along the path of the ray that intersects the projection plane at that point. Generating MIPs along a plurality of viewpoints generally improves volume visualization. MIPs generated along a plurality of viewpoints forming a simple curve create the illusion of volume rotation when played back sequentially. For these purposes, the MIP need not be computed in real-time. Background computing and processing of an MIP may identify abnormalities and the UI can automatically notify the operator.

Other intensity projections are known and useful. The most common three real-time MIP displays use viewpoints along the X-, Y-, or Z-axis. The explanation above described the MIP with viewpoint along the Y-axis. This MIP displays an apparent B-scan slowly changing over time. Horizontal or vertical integration of each B-scan forms the MIP along the X- or Z-axis. Thus, for each B-scan of the volume acquisition, projection forms a single line for each of these MIPs. Alternatively, a Minimum Intensity Projection (MinIP) may be formed to extract low-intensity structures from the volume data. Currently, specular noise produces enough dark regions within tissue to adversely impact MinIP is many applications. However, MinIP is useful for viewing truly non-reflective regions and the scope of its usefulness improves as image speckle is reduced. Those versed in the art will readily see other functions that can be applied to OCT volume data along a viewpoint useful for rendering intensity projections of other features within the volume.

Image Analysis

MIP analysis is an example of an image analysis application. Analysis applications perform image analysis on acquired data, and the analysis is available to the user through the User Interface. In some instances, applications automatically select relevant images and analysis for display. Some viewports display single images while others display sequences of images ("cine" or movies). Optionally, simultaneously displayed movies are registered and synchronized. When applicable, display locators overlay one view of the object locating the region displayed in another view.

By design, the analysis portion of the User Interface efficiently displays relevant images to the user and provides access to image analysis tools. For analysis, the UI displays a combination of images including fundus, en-face, processed OCT and OCT images. For OCT image analysis, the UI displays one or more high definition scans along with a collection of sub resolution images, called thumbnails, each of which is associated with a high definition scan or slice. Viewports present OCT images either in full resolution or as partial resolution thumbnails. Registered images can be displayed stand-alone, side-by-side or overlaid. Overlays can be displayed in color or black-and-white and with varying degrees of transparency. Overlays on high definition displays may need to be upsampled to achieve the same sampling density, while overlays need to be downsampled to overlay thumbnails.

The UI supports both image acquisition and analysis. Image data is acquired in scan patterns using a system scan sequence. In most cases, scan patterns are designed so that data is acquired along lines (B-scans) or collections of lines, such as a rasterized volume. Volume scans can be cube, starburst, spiral, or other collections of lines that fill a volume at some resolution. A typical volume image acquisition is a collection of imaging planes that fill the volume.

Figure 2:
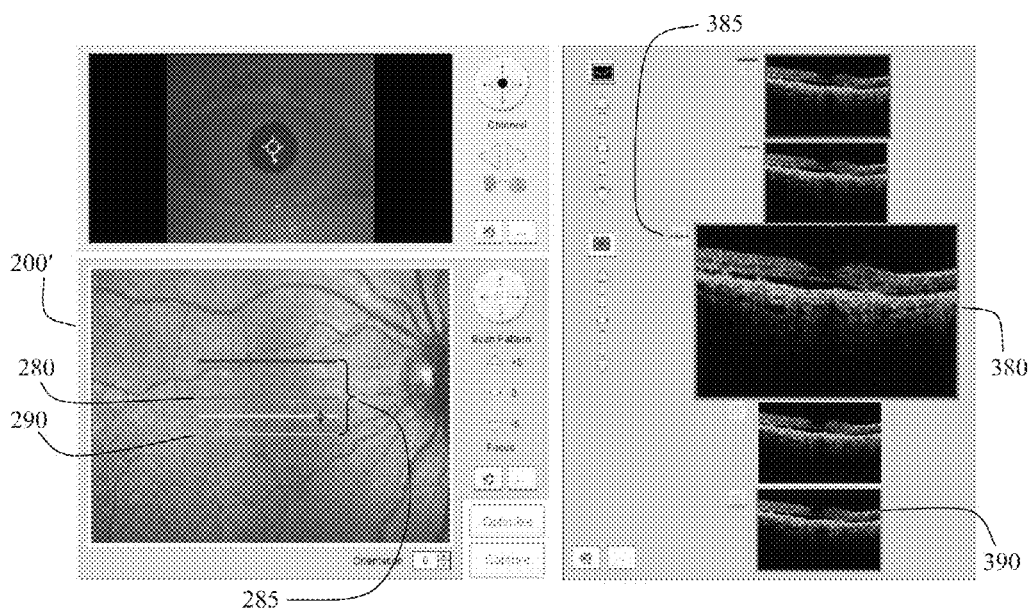
FIG. 2 illustrates the use of a color slice locator to associate the location of a volume slice within the summary image viewport.

In acquisition mode, the UI supports both alignment and review. In FIG. 2, the UI displays the system scan sequence identifier (or scan type) in the fundus viewport 200'. In FIG. 2, the raster scan icon 285 identifies the scan type as a raster sequence. The scan type can be displayed as text or icon anywhere in the display area or be available through a pop-up or pull down, but it is advantageous to display a scan type icon or thumbnail, overlaid on top of one of the image displays so that it is always available but minimally disturbs the image content. However, the user is able to toggle the icon, to hide it so that the underlying image is fully visible. It is advantageous to display one or more scans in full resolution 380 while other scans appear as thumbnails. "Full resolution" here is resolution relative to the display, not the data itself. Displaying the image in full resolution means presenting it in the highest resolution available for this display, window, or viewport. The image data may well have more lines than the CRT has pixels, but presenting the image in the highest resolution window available is termed here to be full resolution. It is also advantageous that the displayed full resolution scan be selectable by interaction with the scan type icon. For example, selecting element 290 from the raster icon 285 causes scan 380 to be reduced in size to a thumbnail while scan 390 is displayed in full resolution and no longer reduced in size. Whether or not selectable from the icon, the scan is preferably identified within the scan type icon 285 by color-coding the relevant element 280 in the scan type icon 285 with the color used in the ID icon 385. Alternatively or in addition, as noted above, the UI may use the same color to highlight the border of the slice display.

Slice Locators

Figure 3:
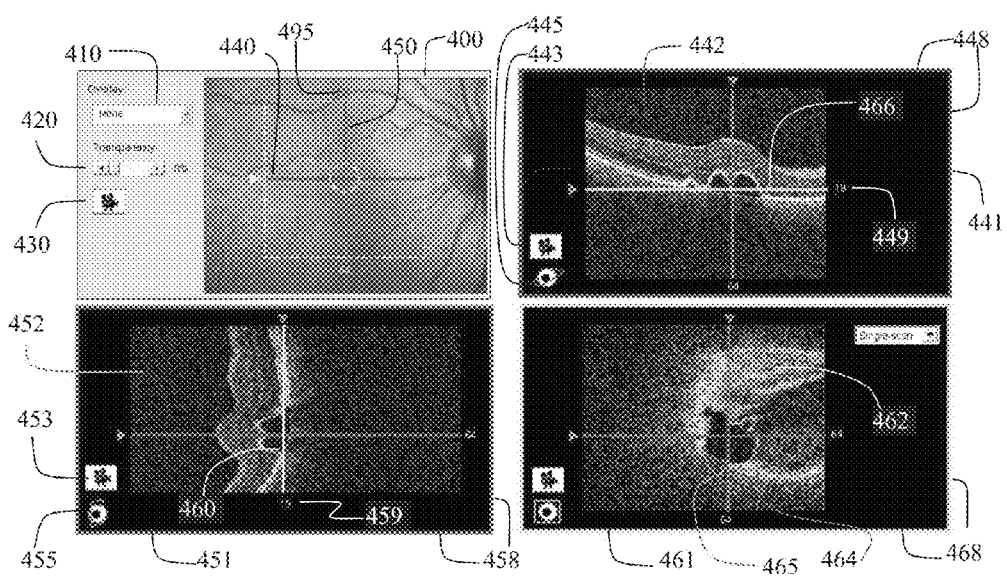
FIG. 3 illustrates the use of color slice locators within the summary (fundus) window and also within each of three perpendicular volume slices.

FIG. 3 depicts an example User Interface for analysis. This UI displays a summary image, in this case an LSO image, and transverse slices of the OCT volume, with locator indicia to help locate the slice of interest. An LSO image 400 is located in the upper left viewport of the UI, providing a summary overview of the eye with anatomical landmarks. Overlays of analysis images on the summary image clarify the anatomy associated with the analysis. The user can access any one of a number of different types of overlays through a drop down menu 410. Common analysis overlays are thickness maps, confidence maps, and OCT en-face images. If the user does not choose an overlay, the UI defaults to overlaying slice locators and an outline of the volume acquisition region on the LSO image. A transparency control 420 allows variable levels of transparency in the overlay. Here transparency means a weighted blending of the overlaying and underlying images. Variable transparency assists the user in clarifying the anatomical location in one extreme and viewing the analysis image in the other.

The UI enables the user to view volume slices individually as still images or collectively as sequences of slices presumptively called movies. A movie play button 430 activates playing the sequence of slices from the current Active Plane. The Active Plane can be horizontal, vertical, or depth. In FIG. 3 shows the horizontal plane in viewport 441, the vertical plane in viewport 451, and the depth plane in viewport 461. Horizontal and vertical slice locators are indicia, indicating the relative location of respective volume slices. The horizontal slice locator 440 and the vertical slice locator 450 identify the location of the horizontal slice 442 and the vertical slice 452. The scan ID icon 445 uses color to identify the association between the slice locator 440 and the slice 442. The scan ID icon 445 further includes graphic information showing that this is a vertical scan. Additionally, the slice border 448 is the same color as the slice locator 440, wherein the color identifies the correspondence between the location in the fundus image and the displayed volume slice. Scan ID icon 445 and slice border 448 are each indicia within the horizontal display viewport indicating that volume slice 442 corresponds to the location indicated by slice locator 440. A play sequence button 443 is associated with the horizontal slices in viewport 441. Activating the play sequence button within the horizontal plane window causes the horizontal plane to become the Active Plane and plays the horizontal slices in sequence, like a movie. As the slices play through the movie, the slice locators in the vertical and depth windows (e.g., slice locator 464 in depth window 461) update the location of the displayed horizontal slice. Similarly, the horizontal slice number is also updated with the movie.

The vertical slice identified by slice locator 450 is located in the lower left viewport 451, here the vertical plane viewport. The scan ID icon 455 again uses color to identify the association between the slice locator 450 and the slice 452. Additionally, the slice border 458 is the same color as the slice locator 450. Clearly, the association between the volume slice 452 and location 450 in the fundus image does not require both indicia 451 and 455. While each presents its own in ease of use value and both may be present, either one establishes the correspondence between image and location. Play sequence button 453 is associated with the vertical slices in viewport 451. Activating the play sequence button within the vertical plane window causes the vertical plane to become the Active Plane and plays the vertical slices in sequence, like a movie. As the slices play through the movie, the slice locators in the horizontal and depth windows (e.g., slice locator 465 in depth window 461) update the location of the displayed vertical slice. Similarly, the vertical slice number is also updated with the movie.

In FIG. 3, depth slices are presented in viewport 461, making 461 the depth plane viewport. A yellow slice locator 460 and the slice number (19) 459 within viewport 451 identify the location of the depth C-scan slice displayed in image 462. Also, a yellow slice locator 466 and the slice number (19) 449 within viewport 441 identify the location of the same depth C-scan slice displayed in image 462. A C-scan is a slice taken from the volume at a fixed depth. The slice border 468 is the same color as the slice locator 460, wherein the color identifies the correspondence between the slice locators in the horizontal and vertical images and the displayed volume slice. Slice locator lines 464 and 465 indicate the location of the horizontal and vertical scans, respectively. Activating the play sequence button within the depth plane window causes the depth plane to become the Active Plane and plays the depth slices in sequence, like a movie. Just as for horizontal and vertical movies, as the slices play through the depth movie, the slice locators in the horizontal and vertical windows (e.g., slice locator 466 in horizontal display window 441 and slice locator 460 in vertical display window 451) update the location of the displayed depth slice. Also, the depth slice number is updated in sequence with the movie.

Selecting a slice locator in any window, typically by moving the mouse pointer over it and clicking, activates it, selecting also the Active Plane. Manipulating the position of the active slice locator, typically by click and drag, causes the corresponding slice to be displayed in the window associated with the Active Plane and updates all other views. That is, when slice locator 466 is selected, the depth plane is selected as the Active Plane. Dragging slice locator 466 to a new slice updates the slice number 449 and image 462 in viewport 461. At the same time, slice locator 460 is updated to the new depth slice location and the depth slice number 459 is updated. Alternatively, entering a slice number (another indicium) selects an Active plane, causes the slice locator to move to a new location, and the causes the UI to display the corresponding slice from that location in the window associated with the Active Plane and update all other views.

For improved viewing of the underlying image, the UI enables the user to toggle the display of slice locators as well as other overlays.

Figure 4:
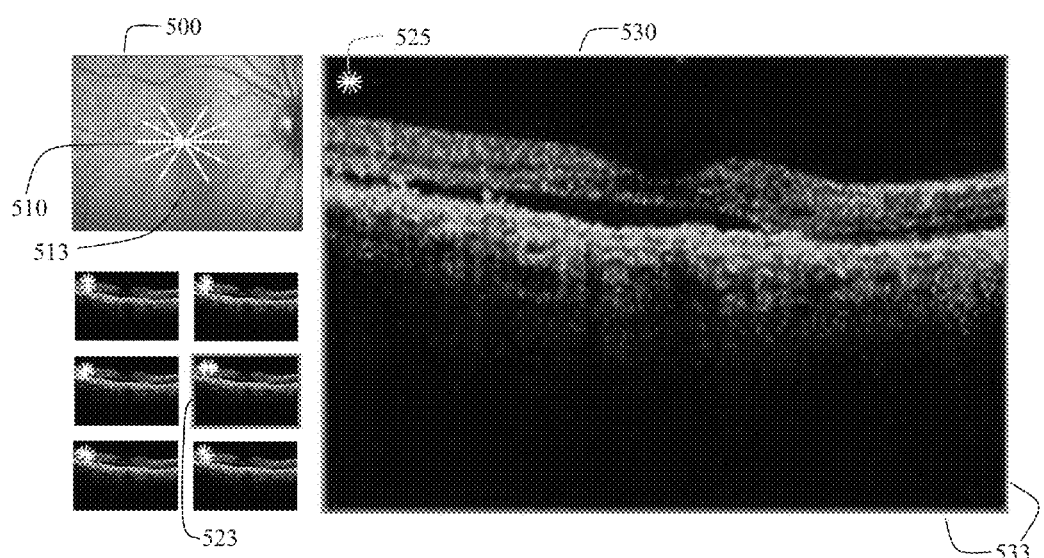
FIG. 4 illustrates a user interface for starburst scan data acquisition.

In FIG. 4, we see an example of the analysis interface images for a starburst pattern. An LSO image 500 is in the upper left of the viewport. The starburst scan type icon 510 overlays the LSO image with slice locators showing the locations of the starburst B-scans of the OCT volume. All six slices of this starburst pattern appear as thumbnails, with the B-scan displayed in thumbnail 523 from location 513 also appearing as a full resolution image 530 on the right. The B-scan display includes an icon 525 associating the displayed image 530 with the corresponding location from which the B-scan was acquired. Icon 525 is a possibly decimated copy of the icon 510 displayed in the LSO window. Because icon 525 may be too small to observe the scan locator within the icon easily, it is advantageous to display a border 533 about B-scan 530 that is the same color as is the border of the selected B-scan's displayed thumbnail 523.

Volume Scrolling

Figure 5:
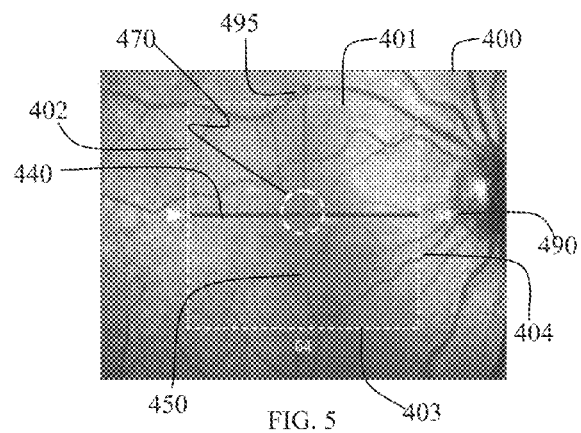
FIG. 5 illustrates additional slice location information that can be displayed in the fundus viewport.

The UI provides a number of features to enable users to scroll through volume data. FIG. 5 shows an LSO image with horizontal 440 and vertical 450 slice locator indicia. Elsewhere, images extracted from the locations marked are displayed. The color of the slice locator matches the color of the border of the matching slice's border within its viewport (not shown here). The dashed lines 401, 402, 403, and 404 indicate the boundary of the acquired volume. The identified volume slice number is displayed beside horizontal slices (as illustrated by 490) or below vertical slices. Users can update the slice locators (and the corresponding displayed slices) by clicking within the LSO image (the intersection of the slice locators moves to the click point), or by clicking and dragging one of the slice locators. In addition, the Active Plane Indicator 495, the colored arrow to the left or above a slice locator, defines which slice locator is "active". Users activate a plane by clicking on its slice locator or active plane indicator. Users can then scroll through the active plane using the mouse's scroll wheel (not shown) or by playing the sequence of scans in a movie by activating the movie button (not shown). Placing a fovea marker 470 over the location of the fovea may help orient the user.

Movie Mode

When simultaneously displaying a summary view and a sequence of B-scans or slices as a movie, the UI synchronizes the movie with the slice locator in the summary view so that the correct slice locator displayed in the summary view corresponds to the volume slice displayed in the movie. When the UI plays two or more movies of volumes acquired for the same patient during separate visits, their volumes can be registered and synchronized before playing. Generally, users prefer to view the movies simultaneously, where side-by-side displays show similar regions of anatomy. However, for some cases, it is easier to see anatomical difference when the UI presents the movies sequentially, in particular, sequentially interleaved.

Volume registration can be global, regional, or local. A global registration of the volumes provides the best single co-ordinate transformation associating the two volumes, but may be inappropriate if there is eye movement in one or both volume images. When artifacts are present in one or both volume images, such as those caused by eye movement, it is often better to identify and remove the artifacts before registering the volumes. Alternatively, if the artifacts are identified, but not removed, the volumes can be registered by separately registering regions within the volumes where there are no (or limited) artifacts. Alternatively, deformable registration of the volumes may account for motion artifacts.

The movies from separate visits are registered and synchronized. When played, synchronized movie frames display volume slices showing corresponding regions of anatomy. Because motion artifacts can create discontinuities in the volume data, it is often best to perform volume registration region-by-region or even slice-by-slice, rather than having a single registration offset for the entire volume. A movie may be played back in slow motion or at high speed. That is, the UI provides for variable rate movie playback. The UI also provides for variable playback frame rate between scans. In one instance, the movie is slowed down when displaying slices from the central region of the volume (generally the region most interesting to the user) and played faster for the first and last slices of the slice sequence (when fewer details of interest are generally observed.)

LSO Cine—Integration of Signal Between Depths

Multiple fundus images are acquired during the exam. Since the LSO scan rate is faster than the OCT volume scan rate, several LSO scans are acquired during an OCT volume scan. For some exams, it is advantageous to combine LSO images before display in order to achieve improved image quality. Noise in the LSO images can be reduced by temporally averaging the images. This smoothing can be performed over disjoint sequences of LSO images, with the accompanying reduced sampling rate. However, the sampling rate can be kept constant, either using an IIR filer or by using an FIR filter with a time-late display. The simplest such FIR filter is the boxcar filter, where a fixed number of LSO images are averaged. Still other combinations of LSO images can be used to improve the LSO image display.

Measurement Tools

Figure 6:
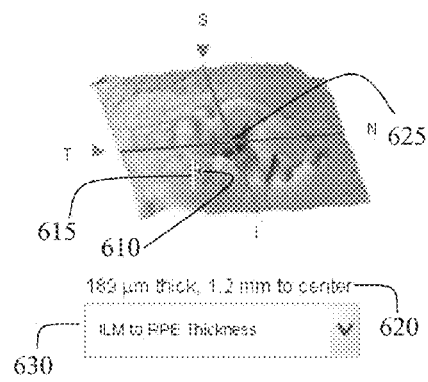
FIG. 6 illustrates measurements on a thickness map.

The UI provides access to measurement tools. The simplest measurement tool is the distance measurement tool, which measures the pixels or voxels between two specified points in an image and converts this measurement to distance units. Other measurement tools are perimeter tools, area tools and volume tools. The Thickness Measurement tool is a particularly important distance measurement tool. FIG. 6 illustrates a thickness map.

Thickness Measurement

Users access the Thickness Measurement tool through the UI in analysis mode. The Thickness Measurement tool, shown in part in FIG. 6, allows the user to determine the retinal thickness at any point on the retina within the OCT volume. By moving the pointer 610 over the thickness map image within the Thickness Measurement tool (accessible from the Toolbar in the UI in analysis mode), the user determines the location to analyze and the Thickness Measurement tool determines the distance from the location to the center of the fovea and the retinal thickness at the location. When a mouse-over pointer is detected on any 3D map, a line 615 is projected from the pointer tip perpendicular to and intersecting the surface of the map. This line and surface intersection point are displayed simultaneously on all maps (although only the intersection is shown on 2D maps such as those overlaid on LSO images). The thickness at the point located is displayed 620 in a popup text string below each map. The popup string 620 displays the thickness at 610 and the distance from the point 610 to the center of the fovea marker 625. These values update as the user moves their mouse over the map surface. When the mouse leaves the map, the thickness and distance measurements disappear.

The Thickness Measurement tool measures retinal thickness from one retinal layer to another. Various authors and investigators use different retinal layers to determine retinal thickness. The Thickness Measurement tool allows for different retinal thickness measurements using a drop down menu 630 from which the user can choose from a variety of thickness measurement definitions. The choice displayed in FIG. 6 is to measure thickness from the ILM layer to the RPE layer. Alternatively, one might choose to measure a portion of the retina, such as the nerve fiber layer thickness. Other choices for measuring the thickness within the retina may be included in this interface.

Patient Information Area

The UI also provides access to the Patient Information Area. The Patient Information Area is a page containing basic information, including such items as: Patient Name, Patient ID, Gender, DOB, Ethnicity, Doctor, Acuity, HIPAA information, exam specific information such as eye examined, reason for exam and diagnostic information, and other patient specific information. The exam study archive includes Patient Information. The system also stores re-exam specific information for the specific patient in the patient exam archive. Re-exam information is information such as the headrest configuration and alignment settings needed to reposition the patient automatically during a second or later visit. For instance, the system records the location and orientation of the headrest components for the exam. This includes the setting of the vertical and lateral position of the chin cup, the tilt angle of the headrest mechanism, the refractive error correction to focus the retina, the depth range setting to center the B-scan, and the polarization compensator setting. Thus for each patient the system stores the alignment parameters necessary to re-align the patient at a return visit. For example, the saved parameters could be: the distance from forehead to chin, the depth from the forehead to the vertex of the eye, the horizontal distance from the centerline of the head to the eye, the refractive error, eye length, and corneal birefringence (the dominant effect on polarization setting). These system settings can be restored on a second or later visit, saving time in system set-up and alignment.

Exam Archives

Figure 7:
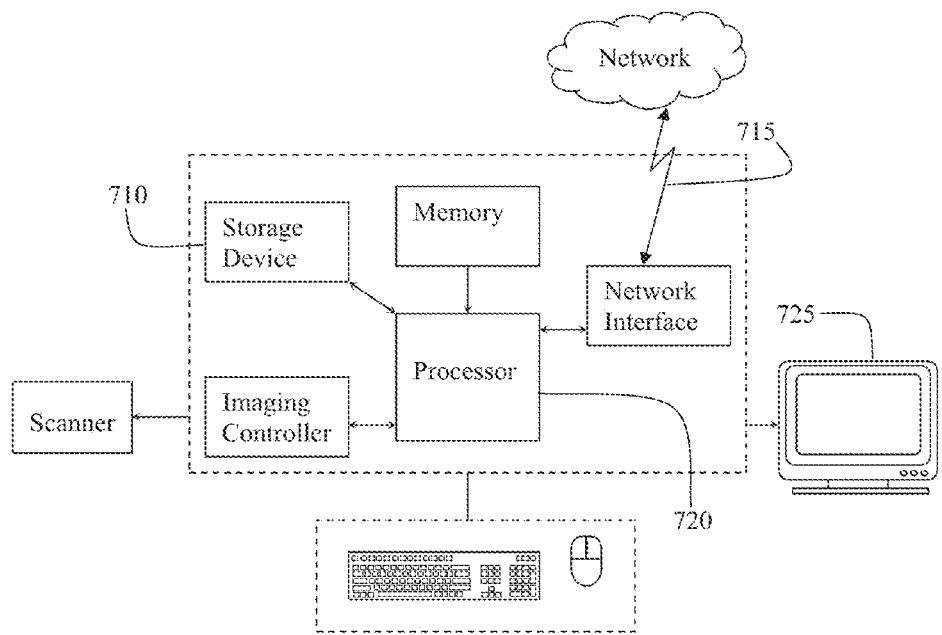
FIG. 7 illustrates a networked system that can store and retrieve exam data either internally, or across a network from another system or from a data server.

The patient exam archives may be subsequently retrieved for further analysis, for comparison to another exam, or for some other reason. The UI provides an interface to search the patient exam archives and retrieve archived exams and studies. Studies are multiple exams linked together by a user because of common characteristics such as patient or disease. FIG. 7 illustrates an exam imaging system capable of archiving exams. Patient exam archives can be on the local machine 710, on another machine networked 715 to the current machine. The networked machine can be another imaging system, a central exam storage server or any other machine capable of archiving data and accessing a network. The UI implements exam archive management functions such as: exam retrieval, database synchronization, archival of exam studies, archive searches and other data archive management functions. The UI can implement user authorization checking before performing archive functions. The user can perform searches based on patient information, doctor information, exam information, diagnosis, or other relevant information. The UI includes a summary page where for rapid review of current and archived exams in various formats. The UI provides exam summaries in text fields (name, date, etc.) and/or by image thumbnails. Archived information includes patient set up information. Using patient set up information, the patient is quickly repositioned on subsequent visits (as discussed above).

In response to an action by the user, the UI will interact with the processor 720 to find all visits (or some portion of all visits) satisfying some search criteria. For example, using a single action, the user may request all exams performed on a specific patient and the UI will display a registered image from each visit on screen 725. Factors determining which exams are available include the type of analysis performed, the availability of data, the operator's access privilege, and limitations in local storage.

Thumbnail

UI display space is limited. Exam thumbnails can be extremely helpful in summarizing a particular exam and finding it within a large collection of exams. In some cases, a search using patient information, doctor information, or diagnosis is quite successful. In other cases, it is useful to see some typical image data from the exam or study. Image thumbnails summarizing the exam simplify exam retrieval. Image thumbnails are stored with the exam and displayed in the exam retrieval UI. Image thumbnails may be automatically chosen, such as a retinal thickness map, or the user may identify one or more images that specifically identify the exam and the UI will make thumbnails of them for exam identification. Users can readily ascertain exam details by viewing one or more of the exam thumbnails. Hyperlinks or other active links associate thumbnail images with the originating exam or study. Executing the link of an exam thumbnail retrieves the desired exam or displays the desired view. For example, a thumbnail image could be a maximum intensity projection along the fast scan axis, along the slow scan axis, or along the depth scan axis. Alternatively, the thumbnail might be a fundus image, OCT en-face image, a thickness map image, or a B-scan image.

Composite Thumbnail

Figure 8:
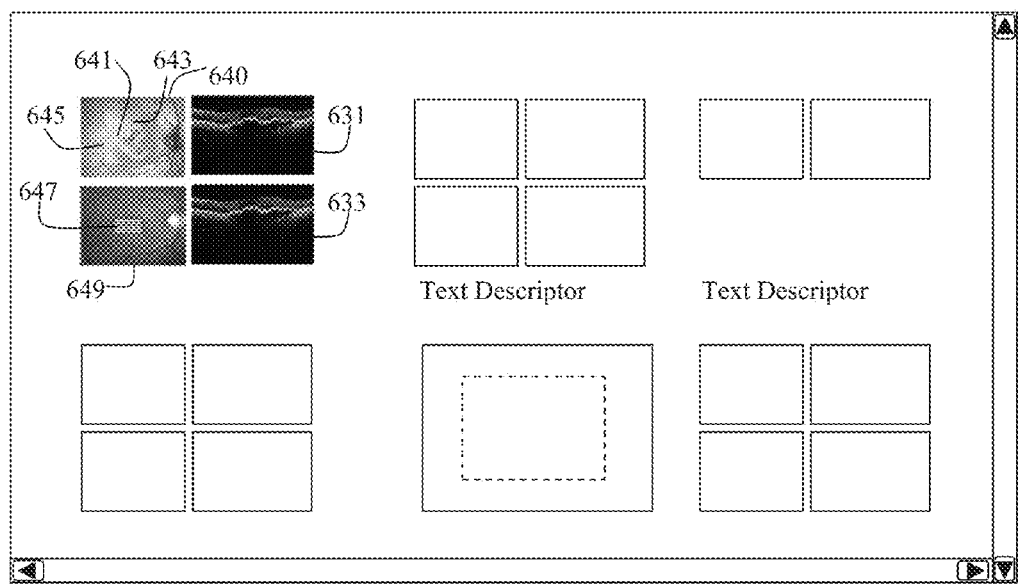
FIG. 8 illustrates an exam retrieval interface with a combination thumbnail containing a fundus image with analysis overlay, and en-face image with scan-type icon overlay and two thumbnail B-scan images used for exam identification.

One available thumbnail summary is the composite thumbnail shown in FIG. 8. The composite thumbnail is a summary indicator that combines, in a thumbnail, various components of the actual data set in a reduced resolution format. A composite thumbnail is a thumbnail composed of a collection of thumbnails. A composite thumbnail is often composed of thumbnails of different display types or formats, such as B-scans, OCT en-face, fundus, or analysis maps. FIG. 8 is a cartoon of a collection of composite thumbnails displayed on a screen. FIG. 8 shows one actual composite thumbnail, with placeholders for many on a page. Each composite thumbnail is associated with an exam or an exam analysis and double clicking on the composite thumbnail can retrieve the associated exam or analysis. The composite thumbnail shown in FIG. 8 combines an LSO image 640 with thickness map overlay 645. It also includes slice locators 641 and 643 indicating the location of 2 tomograms. Also included in the composite thumbnail is an OCT en-face image 649 overlaid by a scan type icon 647, in this case indicating a raster scan. The two thumbnails 631 and 633 on the right of the composite thumbnail are thumbnails of the two tomograms indicated by 641 and 643, respectively. Display resolution and real estate limit the size and number of composite thumbnails presented. The simplest composite thumbnail, not counting a simple thumbnail, is a decimated image with overlay, such as an LSO with thickness map overlay or an OCT en-face with exam type indicator overlay.

Control Elements

Figure 9:
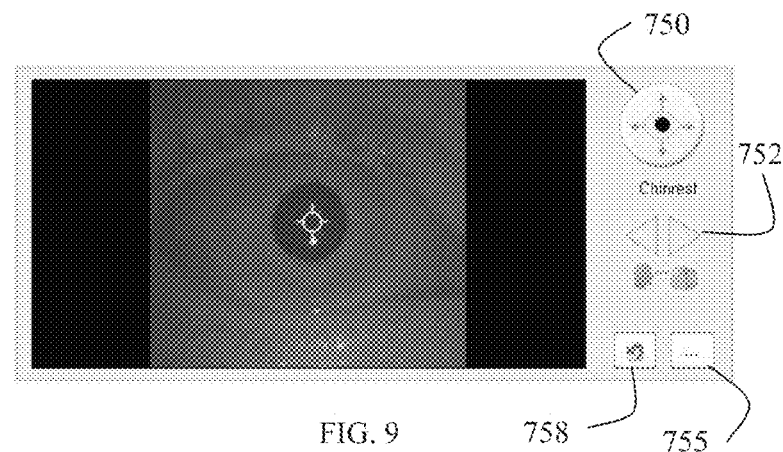
FIG. 9 illustrates system alignment controls located in the Iris viewport next to the image display.

For user convenience, when space allows, the UI has some control elements embedded in the viewport. For example, the Iris viewport has available space on most display devices since the Iris display itself is square and most display devices are wider than they are tall. As shown in FIG. 9, the chinrest controls 750, focus control 752, and button 755 providing access to other controls are located in the Iris viewport near the Iris display. Button 755 provides access to additional controls, such as brightness and contrast controls. Alternate controls, including hard key controls, can replace soft controls displayed in viewports. For example, the chinrest and focus controls, may be hard key controls or soft key controls accessed via a viewport without display images. The UI default disables the Iris reset button 758 until an adjustment is made. While other implementations are possible, the location of the controls is easy to find and natural for most users, simplifying user training. In another instantiation of this interface, the user accesses the controls through menus or pop-up windows accessed by clicking on a control location. In yet other instantiations, the user accesses the controls through menus or pop-up windows available through context sensitive cursor sensitive graphics areas, where the action of the interface device is dependent upon the content of the display area.

Figure 10:
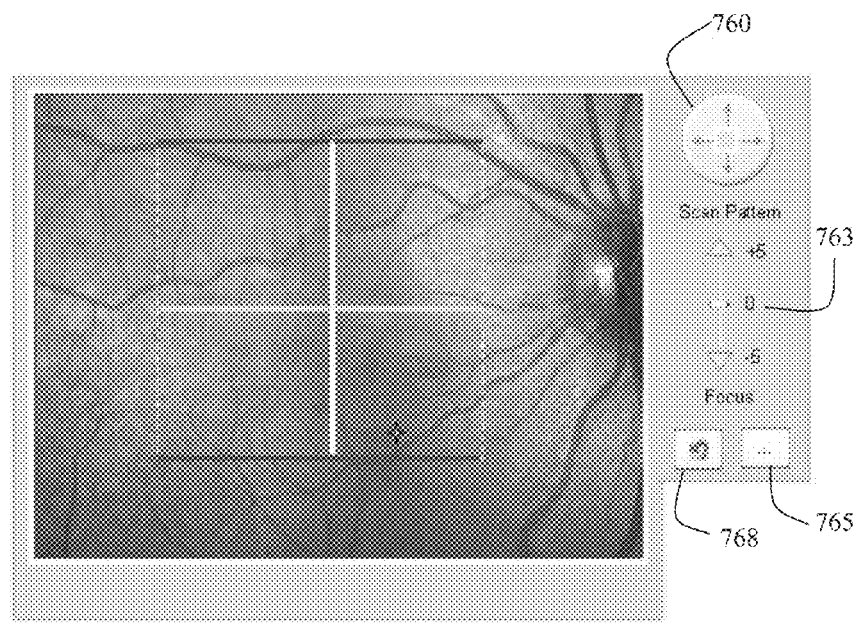
FIG. 10 illustrates system controls located in the fundus viewport next to the image display.

FIG. 10 is a display of the summary (LSO) image Viewport with UI controls embedded in the display. A user adjusts the horizontal and vertical volume acquisition region by means of a 2-D motion button 760 while slider 763 controls the focus. Button 765 provides access to other controls such as brightness and contrast. The LSO reset button 768 is nominally disabled until an adjustment is made. Embedding UI controls in the analysis UI viewport simplifies user access and training. In other instantiations of this interface, the UI controls do not require real estate in the analysis UI, e.g., UI controls are accessed through a pop-up or drop-down by clicking on a control button or activated by placing the cursor in a context sensitive area activating the control pop-up window or drop down menu.

Image Registration

Figure 11:
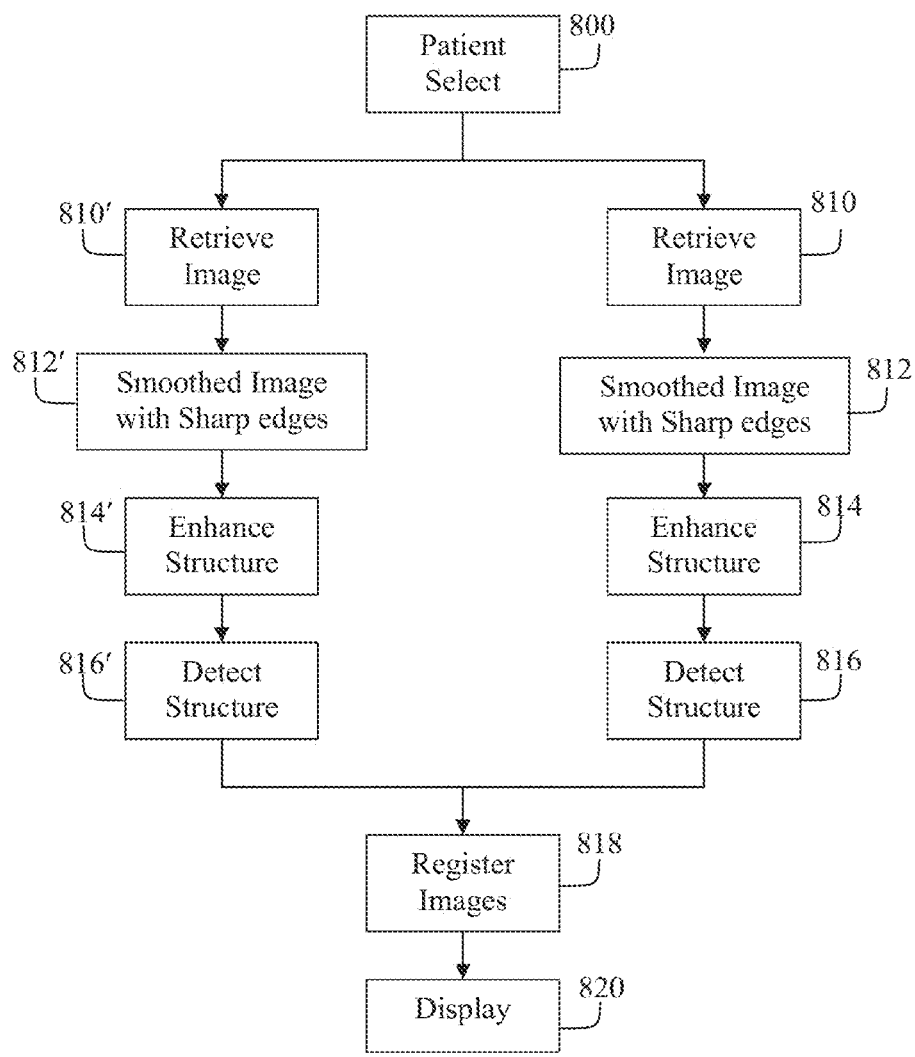
FIG. 11 is a flow diagram illustrating a method of registering one image to another.

FIG. 11 is a flow diagram illustrating a method of registering two images. These images are from the same patient 800, of the same view, and the same eye; but are acquired at different times. One image of a current exam may be retrieved 810 from either memory or local hard drive or both images 810 and 810' may be retrieved from the local hard drive or network storage. Image registration gives us a common coordinate system between the two images. After registration, when we look at corresponding locations in each image, we know that we are also looking at the same physical location in the patient's retina.

Images of the same eye generally have the same underlying structure, such as the retinal vasculature, which is consistent over time. Underlying structure in each image is detected in 816 and 816', and these underlying structures are matched and aligned to each other 818. Registering the underlying structure of one image to the underlying structure of the other registers the images to one another.

The underlying structure we are interested in is the vasculature of the eye. First, we smooth 812 and 812' the speckle while preserving the edges of the underlying structure. There are many mechanisms for smoothing speckle such as filtering, using boxcar filters, with the inherent image artifacts, or smoothing with other low pass filters, like Gaussian filters, with somewhat fewer artifacts. Edge blurring is inherent in these methods. High pass filters can enhance edges, creating their own inherent image artifacts. Well known methods, such as those developed by Sobel, Canny, Haralick or others (see Pal, N. R. et al., Pattern Recognition, Vol. 26, No. 9, 1277-1294), can be used to detect edges. After edge detection, resolution of vessel interior can be problematic in target rich environments with large numbers of vessels, especially if the vessel sizes vary. Time permitting, techniques like Perona and Malik's anisotropic diffusion (see Perona, P., Malik, J., IEEE Trans. Pattern Analysis and Machine Intelligence, Vol. 12, No. 7, 629-639) or Yu's speckle reducing anisotropic diffusion (see Yu, Y., Acton, S., IEEE Trans. On Image Processing, Vol. 11, No. 11, 1260-1270) provide improved performance by smoothing interior regions while preserving edges. Indeed, any filter capable of smoothing speckle noise from optical imaging data without blurring edges is likely to find application here, especially anisotropic filters, with independent smoothing and edge preservation in different directions.

Smoothing the image without significant blurring of edge boundaries provides some enhancement of underlying structure. Further enhancement is needed for some images. Smoothing without edge retention reduces vessel wall contrast, reducing the detectability of the underlying structure. Depending on the underlying structure and background noise levels, gamma correction may be sufficient for enhancement. However, in general, a structure enhancement 814 and 814' process is more robust. It has been demonstrated that the eigenvalues of the Hessian of the image data can be used to enhance tubular regions within an image. The eigenvalues of the Hessian derived from regularized derivatives are known to be more stable. Regularized derivatives are derived by convolving the image with the derivatives of a Gaussian kernel of appropriate scale chosen by choosing the σ of the Gaussian. Frangi (in Frangi, A., et al., IEEE Trans on Medical Imaging, Vol. 18, No. 10, 946-956) and Sato (in Sato, Y., et al, Medical Image Analysis, 2(2):143-168) have demonstrated this technique for enhancing tubular regions, with emphasis on enhancement, and binarization, respectively.

Once the underlying structure is determined in both images, these underlying structures are represented as images 816 and 816' that are registered to each other. Typical registration techniques use rigid registration to register equally scaled images. Elastic registration techniques register images that are not equally scaled. Underlying structure images are registered either using a single process or staged using a coarse-fine registration technique. Coarse-fine registration obtains the final registration result in stages. In the first stage, decimated images are registered. Registering decimated images reduces the computational complexity by reducing the registration search space. This is the coarse registration. Fine registration then registers the high-resolution images. The fine registration also has a reduced search space, because the coarse registration sets a starting point and bounds the search extent. Correlation, sum squared difference, sum absolute difference, Bayesian maximum likelihood, and/or cost function metrics can be applied to create a measure for choosing the best-matched registration. Once the underlying structures are registered, the original images are themselves registered to each other.

The resulting registration can be displayed using different color channels for each image of the registered pair. The vessel enhanced binary or grayscale images can be converted from intensities of white to intensities of a unique color (preferably a color channel color) allowing their overlay to be more easily visualized. In this fused display, vessels that are properly registered overlay perfectly and take their color from both color sources (or channels), forming a new color, while vessels that are not properly registered do not overlay each other and appear in the combined image in their original color. In this display, the quality of the registration is immediately apparent to the viewer.

Intelligent Data Review

Figure 12:
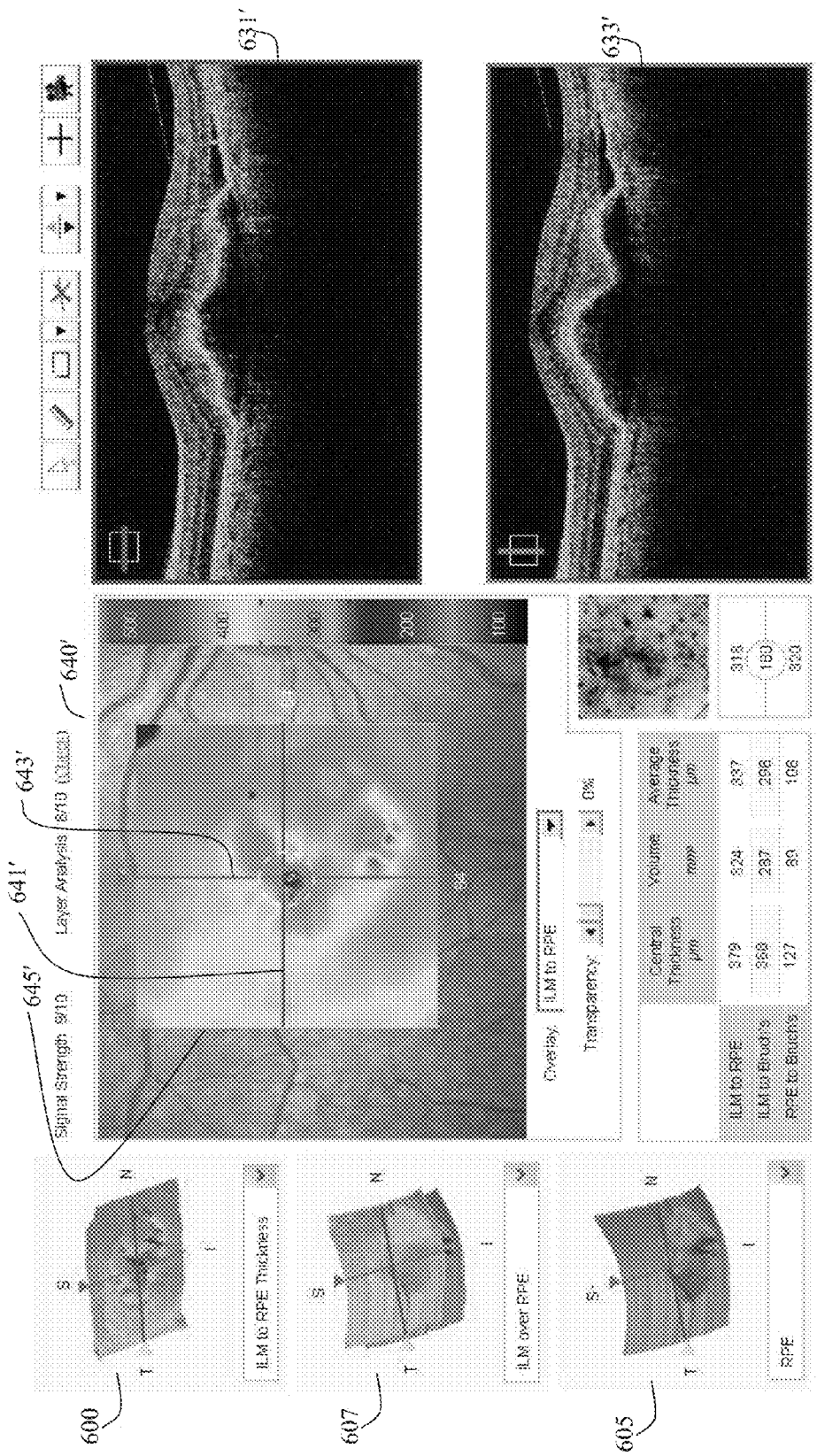
FIG. 12 illustrates a user interface display for thickness maps. The thickness map is displayed, along with the upper and lower surfaces used to compute it. The thickness map is overlaid on an LSO map and multiple volume slices of the OCT volume scan are displayed.

There is a distinct need in the field to display relevant information in an efficient manner. FIG. 12 illustrates a user interface displaying relevant information in an efficient manner. A summary image 640' (in this case an LSO fundus image) is registered to a thickness map 600, which is overlaid 645' over the fundus image 640'. The thickness map is itself registered to the volume. A region of interest (ROI), in this case the fovea, is identified within the LSO image (or the thickness map); and the appropriate horizontal and vertical slices of the volume are located (641' and 643'), extracted from the volume and displayed 631' and 633', respectively, showing the region of interest within the volume. As shown in FIG. 12, the summary image data 640' and volume data (not shown) do not have to be acquired by the same imaging device or by the same subsystem within an imaging device, but they do need to represent the same region. Because the summary image is registered to the volume, the relevant slice of the volume associated with the ROI in the summary image can be extracted from the volume and displayed. Not only is the relevant slice of the volume readily available to the user, but also the thickness map overlaid over the fundus image efficiently displays the metric (thickness) within the context (fundus image).

Also shown in FIG. 12 are images showing the upper and lower surfaces from which the thickness map is computed. In this case, image 600 is the thickness from the internal limiting membrane (ILM) to the retinal pigment epithelium (RPE). Item 607 shows the ILM over the RPE. Since the RPE is mostly hidden in this image, item 605 clarifies the RPE image by showing the RPE surface alone.

Figure 13:
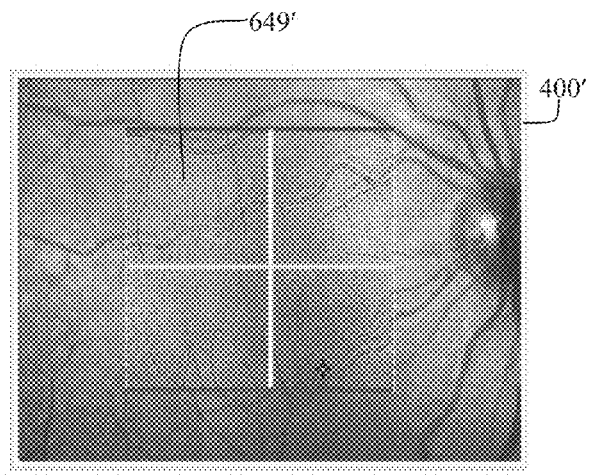
FIG. 13 illustrates an en-face overlay over an LSO image.

As described above, the identified ROI within the image need not be directly registered to the volume. Rather, the identified ROI within the image may be indirectly registered to the volume through one or more intervening registrations. For example, an OCT volume and an en-face image derived from it are inherently registered. FIG. 13 illustrated an en-face image overlaid over an LSO summary image. In this example, in order to improve visualization of the overlay, the en-face image is slightly misaligned and transparent, so that the difference in the images is more readily visible. An en-face image 649' and an LSO image 400' are registered. Registration may be accomplished through common image device coordinates, through image processing image registration techniques or by manual manipulation. Identification of a region of interest like the fovea within the LSO image identifies one or more slices through the fovea within the volume. In many cases, the horizontal B-scan of the OCT volume through the fovea is the preferred slice because it is the slice acquired requiring the least time for acquisition. The horizontal B-scan is the volume slice least likely to be compromised with motion artifacts. In other imaging systems with different scan sequences, this minimal time slice through the fovea may be vertical rather than horizontal.

Figure 14:
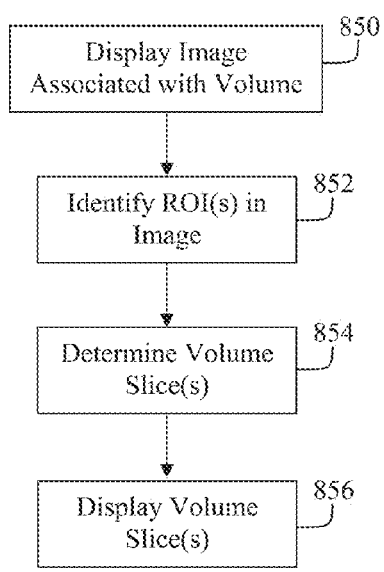
FIG. 14 is a flow diagram of an improved volume slice presentation associated with lesions.

FIG. 14 illustrates another efficient presentation of relevant information, such as automatic identification and display of slices associated with a lesion. Previously, a sequence of slices extracted uniformly from OCT volumes displayed regions suspected of containing retinal lesions. Nominally, the sequence displayed was a sequential sequence of B-scans. By automatically selecting relevant slices for display, we display information more efficiently by showing more data that are relevant in fewer images.

First, we display a summary scan 850. While this summary scan can be an LSO image, it is usually more relevant to display, or at least overlay the display, with a thickness map. Lesions are associated with peaks in the retinal thickness map. As shown above, the derivation of the retinal thickness map registers it to the OCT volume data. Identification of a peak in the thickness map 852 identifies one or more slices 854 of the volume through the peak. While the UI enables the user to choose the peak or peaks in the thickness map manually, there is a strong advantage to having one or more peaks automatically detected. Any one of many peak-picking methods can identify the most relevant peak. While the tallest peak is readily ascertainable, in many instances, the peak supported by the largest volume is of equal or greater importance. The tallest peak, if unsupported by neighboring thickness in the thickness map, may be merely noise.

Particular care must be taken when locating more than one peak. One method for finding secondary extrema is to choose appropriately constrained local extrema, for example, peaks separated by a minimal distance. Another method utilizes a contour map derived from the thickness map. After choosing the first peak, a threshold is set defining a neighborhood about the first peak wherein a second peak cannot reside. One such threshold requires a valley of at least a minimal depth between two peaks. Alternatively, the valley depth might be a function of the peak heights. Another such threshold requires a minimal separation between peaks.

Once the application locates peaks, it extracts and displays 856 one or more slices of the OCT volume through the peaks. Extracted slices showing peaks in thickness are more relevant than equally spaced slices. Nominally, the application chooses B-scans for display, since a B-scan is the volume slice least likely to be compromised with motion artifacts. However, slices chosen to illustrate other features of the lesion, such as breadth or volume may be chosen for more efficient analysis of the lesion.

The format of an efficient image display depends on the anatomy imaged, the analysis conducted, and the content of the images. When the user selects an analysis tool, a display format is selected to display data relevant to the anatomy and analysis. Algorithms within an analysis tool application are designed to detect features or anomalies, or enhance identifiers associated with a specific pathology. For example, in retinal analysis, the thickness map enhances lesion detection and enables automatic lesion detection. Large lesions extend across multiple B-scans. The application identifies the lesion correctly in multiple neighboring B-scans. However, it is redundant to display the same pathology repeatedly. For this reason, tools are designed to segment the volume into specific regions of interest and extract metrics that are indicative of the features of the specified pathology relative to the specific region under examination. Slices representative of the various regions are displayed, or slices specific to a region generally indicative of the extent of the pathology within the region are chosen for display. Display space is limited. A limited number of slices, images, or maps are presented in the UI, usually between two and five, with additional information available using overlays. The UI displays more items when limited resolution is sufficient. When items do not need to be simultaneously available, the UI scrolls one or more images off the viewing area.

Report

Selected images are automatically integrated into a report. The report can be subsequently reviewed, printed, or electronically archived. Automatically selected images can be reviewed, accepted, and/or replaced by manually chosen images selected by the user. Once the report is accepted, it can be archived or printed with a single command.

Automatic Identification of Suspicious Results

There is a distinct need for automatic identification of problematic data and suspicious analysis results. Herein disclosed is a system for automatically identifying and displaying a suspicious segmentation result for review and/or correction. A measure of confidence in a segmentation result is established, estimating the probability of segmentation errors and providing a mechanism to select segmentation results with low confidence for user review. This measure of confidence is called a confidence map. The number, location and confidence of suspect results are determined and incorporated within the confidence map. Some or all of the suspect segmentation results can be displayed for user modification. When automatic propagation of segmentation modifications is enabled, segmentation corrections are propagated within the slice and into nearby slices. Thus, enabling automatic propagation reduces the number of suspect segmentations displayed to the user because only one slice in a cluster of suspect slices needs to be displayed for possible correction.

The confidence map may be generated either during or after the segmentation procedure. In one embodiment, specified steps and portions of the segmentation process are associated with elements of a cost function used to develop the confidence map. Examples of elements associated with the confidence map are: image intensity, local variations in intensity, measure of continuity (or discontinuity) of segmentation results, measures of variation in segmentation depth and other measures of internal segmentation consistency, strength of image gradients, the number of detectable layers or edges, feature shape and orientation, and geometric proximity (say to boundaries of the imaged area and/or segmentation results and other measures of a priori information about the segmentation and the surrounding environment). Both theoretical and heuristic factors are included to improve the precision of the confidence map.

A confidence map is a record of the degree of certainty of the segmentation operation at each point of the segmentation. In one embodiment, the confidence map is a weighted function of confidence metrics. Each confidence metric estimates the degree of certainty of a particular aspect of the segmentation at each point. Confidence metrics can be developed around any of the elements associated with the confidence map. For example, one metric is the intensity of the signal at the segmentation boundary. This metric is generally weighted more heavily for segmentations based on signal strength, such as RPE boundary segmentation, but is not weighted as heavily for segmentations based on image gradients, such as the ILM boundary segmentation. Another metric is the strength of the image gradient at the segmentation boundary. Metrics can be developed for each of the elements mentioned above, as well as for other features used or useful for segmentation decisions. In general, since the physical layers being imaged and segmented are expected to be unbroken, abrupt discontinuities in the segmentation are weighted low in confidence. The greater the discontinuity, the lower the continuity confidence metric is valued. Confidence metrics may be based on the segmentation alone or any combination of segmentation and image data. When more than one feature is being segmented, a confidence metric may be based on any combination of data from one or more segmentation results and image data. For example, when both the RPE and ILM are segmented, a confidence metric combining the two segmentations is the consistency of the segmentations of the RPE and ILM. Another combination metric is the continuity of the measurement of the distance between the RPE and the ILM.

The confidence map is a combination of the individual confidence metrics. For example, when each confidence metric is non-negative, the sum of the individual metrics, or the sum of the squares of the individual metrics, or a normalized, weighted sum of the individual metrics are all instances of confidence maps. For example, one confidence map is a normalized weighted sum of four confidence metrics; $m_I$ (for intensity), $m_D$ (for discontinuity), $m_C$ (for consistency), and $m_G$ (for geometry):

$$\tfrac{1}{2}\{\tfrac{1}{2}m_I + m_D + \tfrac{1}{2}m_C + m_G\}$$

Similarly minima, maxima, medians, products, weighted products, and normalized weighted products of the individual metrics also provide instances of confidence maps. An example of a weighted product of individual measures $m_1$ and $m_2$ is $m_1 \cdot \sqrt{m_2}$ and a normalized weighted product is $(m_1 \cdot \sqrt{m_2})^{2/3}$.

Alternatively, the confidence map may be derived directly from one or more segmentation results either including or without including direct computations on image data. It is not necessary that the confidence map be computed from individual confidence metrics. For example, a confidence map may be the output of a properly trained neural net. The neural net can be trained to recognize segmentation errors from the segmentation results, image data, and a set of training data with segmentation errors identified by an expert.

Comparison of the segmentation and the original image provides additional factors for the confidence metric. Reasoning combines individual measures into the confidence metric by formulas, logic, partial information logic (fuzzy logic) or even neural networks. Many confidence metrics are equivalent and each is dependent upon the threshold at which decision points are set.

When displayed, the confidence map can overlay the thickness map, the LSO or other fundus image, or the confidence map display may stand-alone. The confidence map can be used to modulate a thickness map, another confidence map, or any display of the segmentation. For example, a normalized confidence map can be used for transparency control of a thickness map overlay. In areas of complete confidence, the thickness map is completely opaque, while in areas of no confidence, the thickness map is completely transparent. This overlay provides the user with a visual representation of the thickness map where the segmentation confidence and a transparent view of the fundus where the segmentation confidence is low. Another combination example is multiplying the normalized confidence map of the RPE segmentation by the normalized confidence map of the segmentation of the ILM. This is one example of a confidence map of the thickness estimate. Combinations need not only include combinations with confidence maps. One such combination modulates an en-face image by a thickness map. A new image is formed using the intensity of the en-face image while adding color, where the hue of the new image is proportional to the thickness in the thickness map. Of course, any fundus image can display retinal thickness using any color map by means of a look-up table or other function associating thickness with color.

Summarizing each line of the 2-D confidence map by a statistic of that line projects the 2-D confidence map into a 1-D confidence line. A statistic searching for lines with low confidence could use the minimum value statistic. A mean or median statistic provides an estimate of the average confidence of the segmentation in the line. Such a measure provides an estimate of the confidence that takes significantly less display space. Displaying a confidence line using the minimum statistic along the side of an overlay like the thickness map overlay provides an immediate indication of which slices are likely candidates for segmentation errors. Displaying a confidence line using one statistic along one edge of an image and another confidence line using a different statistic along the opposite edge provides additional information. One such display appends the confidence line derived using the mean statistic along one edge and the confidence line derived from the standard deviation statistic along the opposite edge, providing the user with an estimate of the average confidence of the segmentation within a B-scan and the variance of the confidence within the B-scan with minimal impact on the thickness map display itself.

Intelligent Boundary Editing: Edit-Propagation

Figure 15:
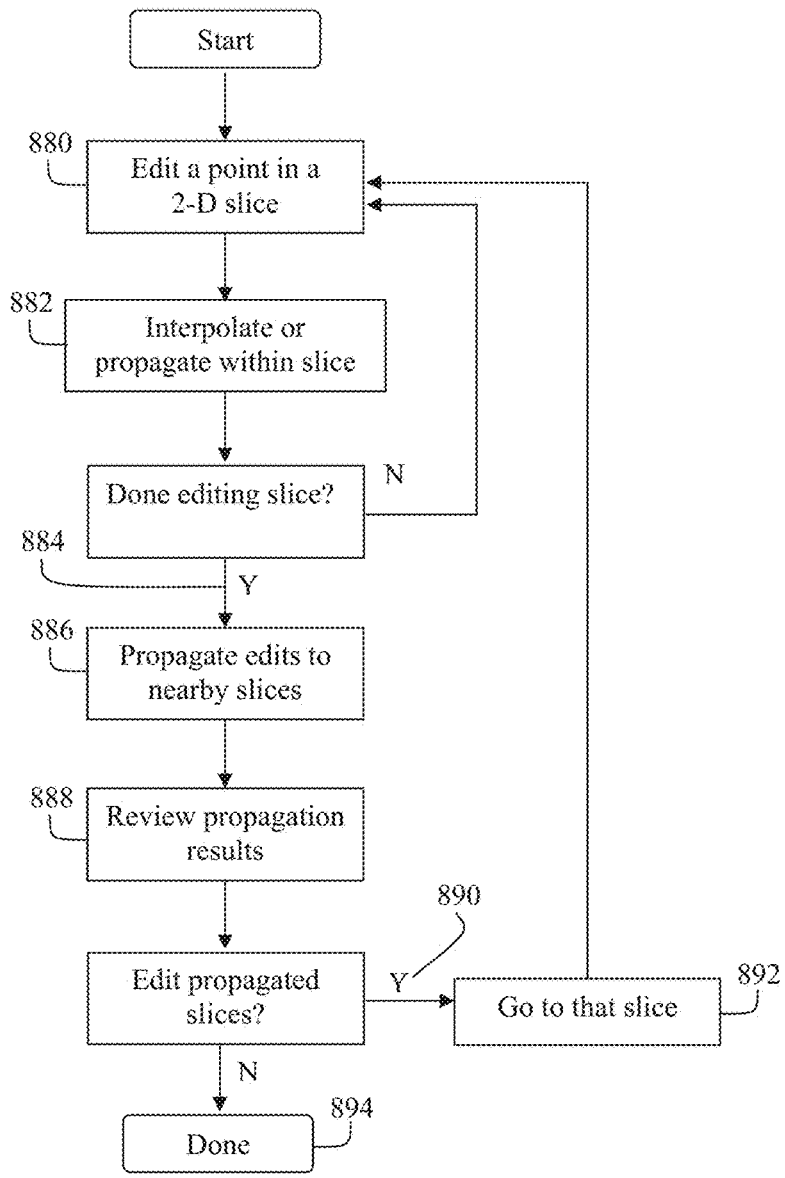
FIG. 15 is a flow diagram of a process for automatic propagation of segmentation modifications.

Nominally, a volume is composed of a collection of B-scans. One segmentation methodology segments each B-scan separately, associating a segmentation confidence with each segmented point of the B-scan. Just as the individual segmentations can be joined to provide a segmentation map, the resulting confidences can be arranged in a confidence map. A suspect point of a confidence map is a point where the confidence map has a low confidence value in a region of interest. A suspect region of a confidence map is a region where the confidence map has low confidence values throughout. When a confidence region is suspect, the segmented image and the suspect segmentation of that image are displayed. It is useful to display both the image and the segmentation in a single viewport, with the segmentation overlaid on the image. For improved visualization of the image, the segmentation overlay can be transparent. The flow diagram of FIG. 15 illustrates this process. If the segmentation appears visually incorrect, the user enables a segmentation editor and modifies 880 the segmentation for that image. When automatic propagation of segmentation modifications is enabled, the automatic propagation application automatically propagates the modification through neighboring image segmentations. It is not necessary to update the confidence map to include the high confidence of the segmentation modification. If the confidence map is updated, the confidence of a manual edit is set very high, ostensibly set to 1, where 1 is the highest possible confidence.

When sufficient information is available within the image, the automatic propagation application recomputes the neighboring segmentation results starting from the known good result provided by the user. Alternatively, when insufficient information is available within the image to create a high confidence segmentation even with the known good result provided by the user, the propagation application propagates the user modified segmentation by interpolation 882 between the user modified region and the region of high confidence. It is also possible to combine interpolation techniques and recomputing segmentation techniques by constraining the segmentation technique to its best result within a neighborhood of the interpolated result. High confidence regions need not be large segments. Interpolation between high confidence regions as small as individual points is useful in extending segmentation boundaries. If there are no local regions of high confidence, the user modified data points can still propagate the modification by smoothing the modification to neighboring segmentation results. Alternatively, the system can display additional regions of low confidence for user modification.

Once the segmentation modification within an image is complete 884, edits are automatically propagated across neighboring images 886. Allowing the local modification to initialize a definite boundary, automatic modification propagation can use the segmentation algorithm to extend the segmentation, using the user modification as a starting point. Alternatively, interpolating between the known good segments can fill a small gap between two high confidence segments of a known continuous object within an image. Extrapolation from high confidence segments can also be used to extend the segmentation boundary. Extrapolation from known good points can also extend segmentation results into regions of low confidence.

When making corrections to the segmentation of a three-dimensional volume of image data, it is helpful to propagate those corrections automatically to nearby regions that require similar corrections. In this way, segmentation corrections require limited, if any, repetitive editing. After the user modification of one or more segmentation points, the automatic propagation module changes neighboring segmentation results in a manner consistent with the volume image contours and in a manner also consistent with the segmentation.

In one embodiment, the extent of the automatic edit propagation (the propagation region) is proportional to the distance of the correction. In this case, for greater correction distances, the automatic modification process will extend its update of segmentation results further away from the edited point. In another embodiment, the extent of the edit propagation is proportional to the distance to the nearest known valid segmentation result. This segmentation result may be known to be valid because it was, itself, a user edit, or it may be known to be valid because the confidence map at this point exceeds a fixed threshold. In an embodiment wherein the confidence map is recomputed for updated points, the edit propagation may extend until the newly computed confidence at a point fails to meet a minimum confidence level. Any of these or combinations of these methods can be used to determine the extent that the edit is propagated. These methods need not be symmetric and will normally depend on the distance between samples in the extension direction.

In one embodiment, an analysis comparing the edited points to the neighboring segmentation results identifies the propagation region. As a first pass, automatic propagation interpolates provisional segmentation results within the propagation region using the edited points and the prior segmentation at the boundaries of the propagation region. Automatic propagation may refine the provisional results, producing new segmentation results that more closely follow the contours found in the image data.

For example, the user is presented a summary image display such as an OCT en-face image, a thickness map, or a 3-D rendering of the layer segmentation. The user selects a B-scan from the image volume and the B-scan is displayed, including the segmentation results overlaying the B-scan image within the selected image display. The user selects one or more segmentation locations within the display, identifying modifications to the segmentation. (If there is only one segmentation layer within the display being reviewed, there is no ambiguity regarding which segmentation is being modified.) If more than one segmentation result is displayed, the user can manually select which segmentation result is being modified, or the segmentation result being modified can be automatically selected by the system, for example, by choosing the segmentation closest the edited point or points.)

In one embodiment, the propagation region is a fixed M×N area where N is the number of pixels along the fast scan direction and M is the number of pixels in the slow scan direction. In another embodiment, the area of the propagation region depends on the size of the modification. In yet another embodiment, the propagation region extends to the nearest high confidence segmentation result in every direction from the modified point. Propagation regions are areas enclosed by discontinuities of the segmentation results. Progressively lowering the threshold used to define a discontinuity establishes a threshold that in turn identifies a region or set of regions containing all of the edited points. The binary image defined by this threshold can be refined by morphological operations, defining a preliminary propagation region. After some refinement by morphological or other processing methods, this binary image defines a region for edit propagation. This region is modified to account for previous user modification that should not be altered, or other specific constraints on propagation, if needed. After accounting for such constraints, the edit propagation region is defined.

Automatic propagation interpolates across the propagation region from edited points to the segmentation surface at the periphery of the propagation region. When the propagation region extends to the edge of the image, automatic propagation extrapolates from the edited point(s) to the image edge in a manner reasonably consistent with both the nearest edited point and the nearby edges of the propagation region. This creates an initial correction to the segmentation over the propagation region.

In the next step, examining the data in the vicinity of the surface refines the interpolated surface. This vicinity may be defined using the differential threshold used in defining the propagation region, by the elevation of the nearest edited points, and/or the segmentation surface elevations along the periphery of the propagation region. Searching in the vicinity of the interpolation, a strong edge (maximum significant axial gradient) in the image typically refines the ILM would, while the maximum significant intensity typically determines the RPE. In the event that there is no significant image information, as in the case of shadows or broad regions without distinct gradients, the interpolation is used for the segmentation correction.

To complete the process, automatic propagation applies post-processing to the segmentation corrections. In its simplest form, automatic propagation smoothes the segmentation result to remove any edges. In some instances, automatic propagation applies a more complex nonlinear process such as high order spline interpolation or median filtering, within the propagation region and possibly extending to the periphery.

An automated editor for propagation of edits is also capable of making imperfect edits. The system includes a capability to review the results 888 of the propagated edits. If another segmentation requires modification 890, that slice and segmentation are displayed 892 and the editing process continues until all modifications are complete 894. An infinitely alternating "limit cycle" of correcting corrections is avoided by ensuring that the manual edits themselves should not be altered by a subsequent automatic propagation of changes.

Choice of Overlay

Analysis results on 2-D and 3-D datasets are often displayed as images, which, for medical imaging, have improved value when they are registered to the anatomy. While the analysis itself is registered to the coordinate system of the data analyzed, the results need to be registered to the anatomical location that they represent in a meaningful way for the user. For most analyses, users have the option of overlaying analysis results on the LSO fundus image. Thickness maps, confidence maps, en-face images, binary images and other images with useful diagnostic information can be derived from the OCT volume data, which is registered to the LSO fundus image. Displaying the analysis results over the LSO image provides context in which to interpret the results. Users can choose the analysis results to overlay and set the transparency of the overlay. Transparency in the overlay enables clearer visualization of the underlying LSO image and better context for the analysis results. Variable transparency allows the user to show more or less detail in the analysis overlay. The ability to toggle the overlay allows the user to view the anatomy and associated analysis in rapid succession.

On a second or later visit, analysis images from previous exams are available and can be overlaid over the current summary image. Any previous LSO, OCT en-face, or analysis image of this patient can be registered with the current exam and can be used to overlay a current summary display. Overlays archived with the exam are available for various applications such as registration and image retrieval. For example, an OCT image from a previous exam overlaid on the current LSO image during pre-acquisition provides a visual indication of a possible misalignment and can be used to help realign the optics to the same orientation as used in the previous exam.

Progression Analysis

Figure 16:
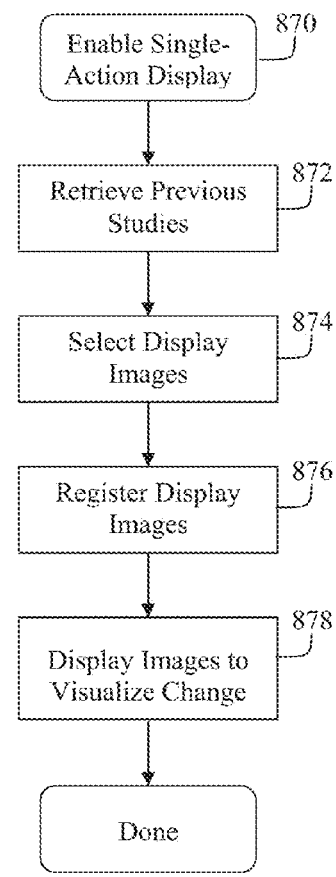
FIG. 16 is a flow diagram of a change analysis process for displaying registered images from different exams.

It is advantageous for medical practitioners to assess changes in tissue over time. The presently described User Interface displays changes in the anatomy of the tissue over multiple examinations. Viewing change over time is useful for monitoring, the progression of a disease or pathology, or the response of tissue to therapy. FIG. 16 shows a flow diagram of a process for displaying registered images from different exams. Initially the system is enabled to acquire data 870. A previous study is retrieved 872 from archive for comparison. If a summary image (OCT en-face or LSO or other fundus-like image) of the previously acquired exam is available, it can be overlaid over the current summary image as described in co-pending U.S. patent application Ser. No. 11/717,263, filed Mar. 13, 2007, publication 2007/0216909, which is hereby incorporated by reference. This enables the operator to position a new scan over the previously scanned area with high degree of accuracy. Alternatively, the system can register the current en-face image to the previous en-face image and automatically position a new scan over the previously scanned area, also described in co-pending U.S. patent application Ser. No. 11/717,263. Once the alignment is complete, the volume acquisition begins. During acquisition, the alignment overlay is replaced by a live display of the OCT fundus image, enabling quality control of the OCT volume scan during volume acquisition. The images to be compared are selected 874 and registering the display images 876 minimizes the remaining differences in acquisition coordinates or anomalies. Corresponding regions of display images from each exam are simultaneously displayed to visualize change 878. As noted above, the side-by-side movie is especially useful for comparing changes in pathologies from visit to visit.

Typically, the first exam performed is the baseline. However, the user can choose any exam in the patient archive to be the baseline exam. Images and image analysis from more recent exams are compared to the baseline exam. When more images are available for comparison than fit on one viewing screen, the additional images are available through a scroll bar or through another image-paging tool. The UI allows the user to reorder images so that the user can compare images in close physical proximity. The system retains the original order so that images can be redisplayed in chronological order, when needed.

Figure 17:
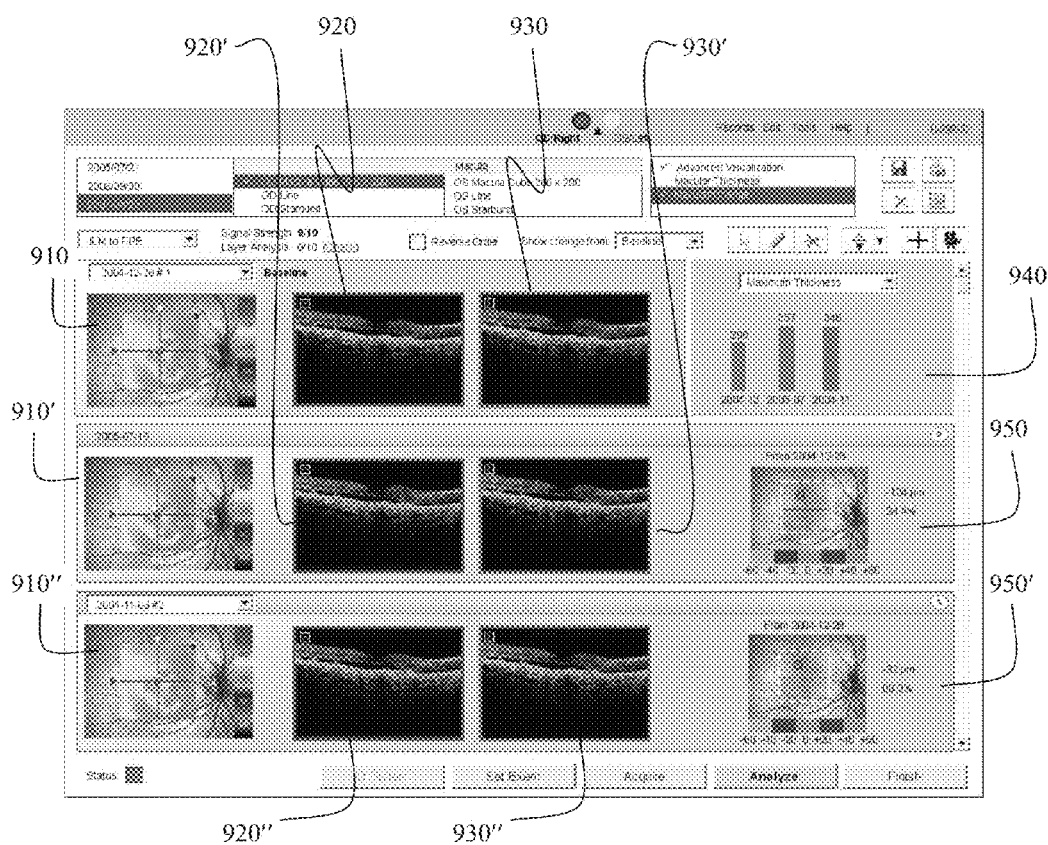
FIG. 17 illustrates an analysis display for visualizing change.

The primary change analysis display, illustrated in FIG. 17, provides a separate row for each exam. On the left side of the row is a fundus image, 910, 910', 910", with one or more tomogram locators. In the center of the row one or more tomograms, 920, 920', 920", 930, 930', 930", are displayed. These are the tomograms indicated by the locators on the fundus image. Different rows display different exams. In order to identify change, the display shows the same areas of tissue in the displays from the different exams. The image data from the different exams are registered, either to data from a single exam, such as the baseline exam, or through a series of connected registrations, such as registering each volume image to the volume image from the previous exam. In this way, multiple volumes are registered either directly or indirectly to other volumes from different exams. The registered images from different exams can be simultaneously displayed. The registration can be done using summary data, such as LSO fundus images registered to en-face images, through direct volume registration, by registering volume regions, or by registering individual B-scans. The UI enables the user to scroll through a selected volume. Synchronization is enabled so that scrolling through one volume scrolls through multiple volumes simultaneously, with registered images from different exams displayed simultaneously. Movies are enabled so that playing the movie for one exam is synchronized with movies playing in another exam.

Other mechanisms for displaying change are also available. When selected, change statistics are displayed. For example, in FIG. 17, maximum thickness change plot is displayed in viewport 940. Of particular interest is any change in the thickness or volume measurements of one or more of the various intra-retinal regions between eye examinations. Users can choose the intra-retinal region of interest (ILM to Bruch's, ILM to RPE, RPE to Bruch's, Region Threshold, User-Drawn Region), and the statistic used to evaluate change (Maximum Thickness, Average Thickness, Center Thickness, Volume). Displays from the region of interest using the chosen statistic are displayed for the multiple visits.

Additional displays are available, such as thickness maps, difference maps, and pathology maps. FIG. 17 displays two pathology map overlays over fundus images, 950 and 950'. The pathology map is an overlay with opaque regions of pathology and transparent normal regions. Choosing an additional display either adds it to the row or replaces a display in the row with it. A difference map between the thickness map of the baseline and the thickness map acquired at a later visit could replace the pathology map displayed in FIG. 17, or be added in a new column, in this case requiring the user to scroll in order that it be visible. A thickness map replacing a fundus image retains the locator feature referencing the location of the slices and the synchronization feature synchronizing the locator with the slices being displayed. Movies remain enabled when the thickness map replaces the fundus image. The various images retain their common co-ordinate system derived through registration of the volume images.

While the description herein describes macular change analysis, the invention is equally applicable to change analysis utilizing image data in other fields, such as glaucoma image change analysis, cataract image change analysis, retinitis or retinopathy image change analysis, and other image change analysis of disease related to the eye or other tissue for which an imaging modality provides a tool for analysis.

Progression analysis measures change over time by monitoring an attribute. The relevance of that change is determined by comparing the measurements either to baseline data or to a model.

Better Measurements of the RNFL

Volume scans make it possible to improve measurements of the Retinal Nerve Fiber Layer (RNFL). A common method of viewing RNFL thickness measurements is to measure the thickness of the RNFL in a cylindrical tomogram centered on the optic disk and plotting the resulting thickness measurements. Misplacement of the cylindrical tomogram creates anomalies in the resulting plot. Since the RNFL is normally thinner further from the optic disk, if the cylinder is displaced from centering on the optic disk, the region of the cylinder further from the optic disk normally measures the nerve fiber layer thinner while the region of the cylinder closer to the optic disk normally measures the nerve fiber layer thicker. Given a 3D volume image of the optic nerve head, one can make a measurement of the RNFL thickness that does not depend on an arbitrary measurement cylinder. The optic disk can be identified within the volume and the proper misalignment avoided. Also, additional data from the volume can be used to statistically improve the measurement data. Additionally, circle scans of different radii can be extracted from the volume data. A study (see Carpineto et al., European Journal of Ophthalmology, vol. 15, no. 3, 2005) has shown that the mean thickness variability is drastically reduced when the size of the ONH was taken into account.

In the cylindrical tomogram, the thickness of the RNFL is determined by segmenting the line at the top of the nerve fiber layer and the line corresponding to the boundary of the retinal pigment epithelium (RPE). For each point on the RPE boundary, there is a closest point to the top of the nerve fiber layer, and the distance to this closest point is a measure of nerve fiber layer thickness. The set of such thickness measures can be plotted as a function of position on the RPE boundary. In the volume scan, the thickness of the RNFL is determined by segmenting the top surface of the nerve fiber layer and the curve corresponding to the boundary of the retinal pigment epithelium (RPE). For each point on the RPE boundary, there is a closest point to the top surface of the nerve fiber layer, and the distance to this closest point is a measure of nerve fiber layer thickness. The set of such thickness measures can be plotted as a function of position on the RPE boundary. The display of the thickness map is a surface. That is, the proposed new measure of RNFL finds the edge of the hole in the RPE where the optic nerve exits the eye. This edge is a curve. The distance from a point on this curve to the segmentation of the top of the RNFL is computed. The average of these distances is a measure of the RNFL thickness in the neighborhood of the ONH. Alternatively, a plot of these distances around the ONH shows the relative thickness about the ONH.

This specification describes various instantiations for efficiently providing relevant image displays to the user. These displays are used to align patients, locate display images within other display images, automatically display suspicious analysis, automatically display diagnostic data, simultaneously display similar data from multiple visits, improve access to archived data, and other improvements for efficient data presentation of relevant information. These disclosures improve diagnostic capability, monitoring and user efficiency.

It should be understood that the embodiments, examples and descriptions have been chosen and described in order to illustrate the principals of the invention and its practical applications and is not intended to be exhaustive or to limit the invention to the precise form disclosed. Modifications and variations of the invention will be apparent to those skilled in the art in light of the above teaching. The embodiments were chosen and described to explain the principles of the invention and its practical application to enable others skilled in the art to best use the invention in various embodiments and with various modifications suited to the particular use contemplated. The scope of the invention is defined by the claims, which includes known equivalents and unforeseeable equivalents at the time of filing of this application.

The following references are hereby incorporated by reference.

US PATENT DOCUMENTS

U.S. Pat. No. 7,084,128, Yerxa, et al., Method for reducing intraocular pressure
U.S. Pat. No. 7,050,615, Avinash, et al., Temporal image comparison
U.S. Pat. No. 7,015,907 Tek, et al. Segmentation of 3D medical structures using robust ray propagation
U.S. Pat. No. 6,771,736, Sabol, et al., Method for displaying temporal changes in spatially matched images
U.S. Pat. No. 6,266,452, McGuire, Image registration method

US PATENT PUBLICATIONS

2006/0030768 System and method for monitoring disease progression or response to therapy using multi-modal visualization
2006/0184014 Registration aid for medical image
2006/0119858 Enhanced optical coherence tomography for anatomical mapping
2005/0238253 Image registration

OTHER PUBLICATIONS

Carpineto et al., Custom measurement of retinal nerve fiber layer thickness using Stratus OCT in normal eyes, European Journal of Ophthalmology, Vol. 15, No. 3, 2005.
Choma, M. A., et al., Sensitivity advantage of swept source and Fourier domain optical coherence tomography, Optics Express, Vol. 11, Issue 18, pp. 2183-2189 (September 2003)
de Boer, J. F., et al., Improved signal-to-noise ratio in spectral-domain compared with time-domain optical coherence tomography Optics Letters, Vol. 28, Issue 21, pp. 2067-2069 (November 2003)
Frangi, A., Niessen, W. J., Hoogeveen, R. M, van Walsum, T., and Viergever, M. A., Model-based Quantitation of 3-D Magnetic Resonance Angiographic Images, October 1999, IEEE Trans on Medical Imaging, Vol. 18, No. 10, pp. 946-956
Gerig, G., Kubler, O., Kikinis, R. and Jolesz, F. A., Non-linear Anisotropic Filtering of MRI Data, IEEE Trans. Pattern Analysis and Machine Intelligence, Vol. 11, pp. 221-232, 1992.
Ishikawa, H., Stein, D. M., Wollstein, G., Beaton S., Fujimoto, J. G., and Schuman, J. S., Macular Segmentation with Optical Coherence Tomography, Investigative Ophthalmology and Visual Science, June 2005, Vol. 46, No. 6, pp. 2012-2017 (2005)
Leitgeb, R. A., et al., Performance of fourier domain vs. time domain optical coherence tomography, Optics Express Vol. 11, No 8, pp. 889-894;
Maurer, C. R., Jr., and Fitzpatrick, J. M. 1993. A review of medical image registration. In Interactive Image-Guided Neurosurgery (R. J. Maciunas, Ed.), pp. 17-44.
Pal, Nikhil R. and Pal, Sankar K., A review on Image Segmentation Techniques Pattern Recognition, Vol. 26, No. 9, pp. 1277-1294. 1993.
Perona, P., Malik, J., Scale-Space and Edge Detection Using Anisotropic Diffusion, IEEE Trans. Pattern Analysis and Machine Intelligence, July 1990, Vol. 12, No. 7, pp. 629-639
Sato, Y., Nakajima, S., Shiraga, N., Atsumi, H., Yoshida, S., Koller, T., Gerig, G., and Kikinis, R., Three dimensional multiscale line filter for segmentation and visualization of curvilinear structures in medical images. Medical Image Analysis, 2(2):143-168, June 1998.

Vermeer, K. A., Vos, F. M., Lemij, H. G., Vossepoel, A. M., 2003. A model based method for retinal blood vessel detection. Computers in Biology and Medicine Vol. 34 (2004) 209-219

Wojtkowski, M., Bajraszewski, T., Gorczyńska, I., Targowski, P., Kowalczyk, A., Wasilewski, W., Radzewicz, C., 2004 Ophthalmic Imaging by Spectral Optical Coherence Tomography, American Journal of Ophthalmology, Vol. 138, Iss. 3, pp. 412-419

Yu, Y., Acton, S., Speckle reducing anisotropic diffusion, IEEE Trans. On Image Processing, November 2002, Vol. 11, No. 11, pp. 1260-1270

Zana, F., and Klein, J. C., A Multimodal Registration Algorithm of Eye Fundus Images Using Vessels Detection and Hough Transform, IEEE Transactions On Medical Imaging, Vol. 18, No. 5, May 1999

We claim:

1. A method of automatically aligning a depth range for obtaining a volume cube scan of a retina of an eye using an optical coherence tomography (OCT) system, said method comprising:
   acquiring two or more B-scans using the OCT system at a first set of system alignment conditions;
   performing image processing on the two or more B-scans to determine a location where the retina would appear in the volume cube scan if the volume cube scan was acquired at the first set of system alignment conditions;
   adjusting the system alignment conditions to optimize placement of the retina within the scan volume;
   acquiring an OCT volume cube scan at the optimized system alignment conditions; and
   storing or displaying the OCT volume cube scan or storing or displaying a further analysis thereof.

2. The method as recited in claim 1, wherein the two or B-scans comprise central horizontal and central vertical B-scans.

3. The method as recited in claim 1, wherein the image processing step includes locating a fovea in the B-scans.

4. The method as recited in claim 1, wherein the two or more B-scans comprise a central horizontal B-scan, a central vertical B-scan, and either two additional horizontal B-scans or two additional vertical B-scans.

5. The method as recited in claim 1, wherein the two or more B-scans are obtained from five regions of the volume cube, the first region being near a center of a depth projection of the volume cube and the four other regions being near edges of the volume cube formed by neighboring cube side walls; and wherein the adjusting step insures that an OCT image of the first region includes a point on the retina farthest from the OCT system and OCT images of the four other regions include four corner points of the retina closest to the OCT system.

6. The method as recited in claim 1, further comprising:
   before acquiring the OCT volume cube, changing a depth location at which the OCT volume cube will be taken;
   acquiring OCT scan data from the changed depth location;
   analyzing the two or more B-scans at a first set of system conditions and the OCT scan data from the changed depth location to discriminate between a real image of the retina and a mirror image of the retina.

7. The method as recited in claim 1, wherein the adjusting step involves moving a fixation target in the OCT system to change a location of the eye in the scan.

8. The method as recited in claim 1, further comprising acquiring one or more high definition B-scans at the optimized system alignment conditions.

* * * * *

UNITED STATES PATENT AND TRADEMARK OFFICE
CERTIFICATE OF CORRECTION

PATENT NO. : 10,362,935 B2
APPLICATION NO. : 15/608239
DATED : July 30, 2019
INVENTOR(S) : Shahram Shawn Dastmalchi et al.

It is certified that error appears in the above-identified patent and that said Letters Patent is hereby corrected as shown below:

On the Title Page

On the page 2, in Column 2, item [56] under "Other Publications", Line 17, delete ""Senstivity" and insert -- "Sensitivity --, therefor.

On the page 3, in Column 1, item [56] under "Other Publications", Line 39, delete "Investigatative" and insert -- Investigative --, therefor.

On the page 3, in Column 2, item [56] under "Other Publications", Line 5, delete "Reflectomety"," and insert -- Reflectometry", --, therefor.

On the page 3, in Column 2, item [56] under "Other Publications", Line 34, delete "Opthalmoscopy," and insert -- Ophthalmoscopy, --, therefor.

In the Specification

Column 2, Line 63, delete "(TOP)" and insert -- (IOP) --, therefor.

Column 2, Line 65, delete "TOP" and insert -- IOP --, therefor.

Column 19, Line 11, delete "filer" and insert -- filter --, therefor.

In the Claims

Column 36, Line 1, in Claim 2, after "or" insert -- more --.

Signed and Sealed this
First Day of September, 2020

Andrei Iancu
*Director of the United States Patent and Trademark Office*